US010987371B2

(12) United States Patent
Chrétien et al.

(10) Patent No.: US 10,987,371 B2
(45) Date of Patent: Apr. 27, 2021

(54) METHODS OF PREVENTING OR TREATING FILOVIRUS AND FLAVIVIRUS DISEASES

(71) Applicants: ADAERATA, LIMITED PARTNERSHIP, Montreal (CA); HER MAJESTY THE QUEEN IN RIGHT OF CANADA AS REPRESENTED BY THE MINISTER OF HEALTH, Winnipeg (CA)

(72) Inventors: Michel Chrétien, Montreal (CA); Majambu Mbikay, L'Ile-Perrot (CA); Xiangguo Qiu, Winnipeg (CA)

(73) Assignees: ADAERATA, LIMITED PARTNERSHIP; HER MAJESTY THE QUEEN IN RIGHT OF CANADA AS REPRESENTED BY THE MINISTER OF HEALTH

( * ) Notice: Subject to any disclaimer, the term of this patent is extended or adjusted under 35 U.S.C. 154(b) by 0 days.

(21) Appl. No.: 16/002,078

(22) Filed: Jun. 7, 2018

(65) Prior Publication Data
US 2018/0353528 A1     Dec. 13, 2018

Related U.S. Application Data

(60) Provisional application No. 62/517,562, filed on Jun. 9, 2017.

(51) Int. Cl.
| *A61K 31/7048* | (2006.01) |
| *A61P 31/14* | (2006.01) |
| *A61K 45/06* | (2006.01) |
| *A61K 9/00* | (2006.01) |

(52) U.S. Cl.
CPC ........ *A61K 31/7048* (2013.01); *A61K 9/0019* (2013.01); *A61K 9/0053* (2013.01); *A61K 45/06* (2013.01); *A61P 31/14* (2018.01)

(58) Field of Classification Search
CPC .............. A61K 31/7048; A61K 9/0019; A61K 9/0053; A61K 45/06; A61P 31/14
See application file for complete search history.

(56) References Cited

U.S. PATENT DOCUMENTS

| 7,745,486 B2 | 6/2010 | Lines | |
| 7,745,487 B2 | 6/2010 | Lines | |
| 8,440,704 B2 | 5/2013 | Lines | |
| 8,901,109 B2 | 12/2014 | Lines | |
| 2016/0151469 A1* | 6/2016 | Ichim | A61K 39/00 424/85.2 |
| 2016/0367517 A1* | 12/2016 | Thompson | A61K 31/353 |

OTHER PUBLICATIONS

Raj et al., Interdiscip. Sci. Comput. Life Sci. 2016, 8, p. 132-141, published online Aug. 19, 2015. (Year: 2015).*

Qui et al., Antimicrob. Agents Chemother., 2016, 60(9), p. 5182-5188, Accepted manuscript posted online Jun. 13, 2016. (Year: 2016).*

Carteaux, G., Maquart, M., Bedet, A., Contou, D., Brugieres, P., Fourati, S., Cleret de Langavant, L., de Broucker, T., Brun-Buisson, C., Leparc-Goffart, I., Mekontso Dessap, A., 2016. Zika Virus Associated with Meningoencephalitis. N Engl J Med 374, 1595-1596.

Furuta Y, Gowen BB, Takahashi K, Shiraki K, Smee DF, Barnard DL. 2013. Favipiravir (T-705), a novel viral RNA Polymerase inhibitor. Antiviral Res 100(2): p. 446-54.

Govero, J., Esakky, P., Scheaffer, S.M., Fernandez, E., Drury, A., Platt, D.J., Gorman, M.J., Richner, J.M., Caine, E.A., Salazar, V., Moley, K.H., Diamond, M.S., 2016. Zika virus infection damages the testes in mice. Nature 540, 438-442.

Johansen L, Brannan J, Delos S, Shoemaker C, Stossel A, Hoffstrom B, DeWald L, Shornberg K, Scully C, Lehar J, Hensley L, White W, Olinger G. 2013. FDA-approved selective estrogen receptor modulators inhibit ebola virus infection. Sci Transl Med 5(190):190ra79.

Julander JG, Bantia S, Taubenheim BR, Minnin DM, Kotian P, Morrey JD, Smee DF, Sheridan WP, Babu YS. 2014. BCX4430, a novel nucleoside analog, effectively treats yellow fever in a Hamster model. Antimicrob Agents Chemother 58(11): p. 6607-14.

Kawiecki, A.B., Christofferson, R.C., 2016. Zika Virus-Induced Antibody Response Enhances Dengue Virus Serotype 2 Replication In Vitro. J Infect Dis 214, 1357-1360.

Lanciotti, R.S., Kosoy, O.L., Laven, J.J., Velez, J.O., Lambert, A.J., Johnson, A.J., Stanfield, S.M., Duffy, M.R., 2008. Genetic and serologic properties of Zika virus associated with an epidemic, Yap State, Micronesia, 2007. Emerg Infect Dis 14, 1232-1239.

Lazear, H.M., Govero, J., Smith, A.M., Platt, D.J., Fernandez, E., Miner, J.J., Diamond, M.S., 2016. A Mouse Model of Zika Virus Pathogenesis. Cell Host Microbe 19, 720-730.

Ma, W., Li, S., Ma, S., Jia, L, Zhang, F., Zhang, Y., Zhang, J., Wong, G., Zhang, S., Lu, X., Liu, W., Yan, J., Li, W., Qin, C., Han, D., Wang, N., Li, X., Gao, G.F., 2016. Zika Virus Causes Testis Damage and Leads to Male Infertility in Mice. Cell 167, 1511-1524 e1510.

Madelain V, Oestereich L, Graw F, Nguyen THT, de Lamballerie X, Mentré F, Günther S, Guedj J. 2015. Ebola virus dynamics in mice treated with favipiravir. Antiviral Res 123: p. 70-77.

Mahmood I, Green MD, & Fisher JE 2003 Selection of the First-Time Dose in Humans: Comparison of Different Approaches Based on Interspecies Scaling of Clearance. J. Clin. Pharmacol., 43 (7), 692-7.

Mansuy, J.M., Pasquier, C., Daudin, M., Chapuy-Regaud, S., Moinard, N., Chevreau, C., Izopet, J., Mengelle, C., Bujan, L., 2016. Zika virus in semen of a patient returning from a non-epidemic area. Lancet Infect Dis 16, 894-895.

Mlakar, J., Korva, M., Tul, N., Popovic, M., Poljsak-Prijatelj, M., Mraz, J., Kolenc, M., Resman Rus, K., Vesnaver Vipotnik, T., Fabjan Vodusek, V., Vizjak, A., Pizem, J., Petrovec, M., Avsic Zupanc, T., 2016. Zika Virus Associated with Microcephaly. N Engl J Med 374, 951-958.

(Continued)

*Primary Examiner* — Jonathan S Lau
(74) *Attorney, Agent, or Firm* — Lavery, De Billy, LLP; Julie Gauvreau

(57) ABSTRACT

A method of reducing the risk of filovirus hemorrhagic fever or a symptom thereof in a mammal host exposed to a filovirus (e.g., Ebola or Zika virus), comprising administering an effective amount of quercetin-3 β-O-D-glucoside (Q3G) or an analogue thereof, or a composition comprising Q3G or analogue thereof and a pharmaceutically acceptable carrier, to said host prior to said exposure.

17 Claims, 19 Drawing Sheets

Specification includes a Sequence Listing.

(56) References Cited

OTHER PUBLICATIONS

Murray, K.O., Gorchakov, R., Carlson, A.R., Berry, R., Lai, L., Natrajan, M., Garcia, M.N., Correa, A., Patel, S.M., Aagaard, K., Mulligan, M.J., 2017. Prolonged Detection of Zika Virus in Vaginal Secretions and Whole Blood. Emerg Infect Dis 23, 99-101.

Nair, A. B., Jacob, S., 2016. A simple practice guide for dose conversion between animals and human J Basic Clin Pharm. 7(2): 27-31.

Oestereich L,, Lüdtke A, Wurr S, Rieger T, Muñoz-Fontela C, Gunther S. 2014. successful treatment of advanced Ebola virus infection with T-705 (favipiravir) in a small animal modeL. Antiviral Research 105:17-21.

Picazo E and Giordanetto F. Small molecule inhibitors of ebola virus infection. Drug Discov Today, 2015. 20(2): p. 277-86.

Qiu X, Alimonti J, Melito L, Fernando L, Stroher U, Jones S. 2011. Characterization of Zaire ebolavirus glycoprotein-specific monoclonal antibodies. Clin Immunol 141(2):218-27.

Rastogi, M., Sharma, N., Singh, S.K., 2016. Flavivirus NS1: a multifaceted enigmatic viral protein. Virol J 13, 131.

Richner, J.M., Himansu, S., Dowd, K.A., Butler, S.L., Salazar, V., Fox, J.M., Julander, J.G., Tang, W.W., Shresta, S., Pierson, T.C., Ciaramella, G., Diamond, M.S., 2017. Modified mRNA Vaccines Protect against Zika Virus Infection. Cell 168, 1114-1125 e1110.

Sakurai Y, Kolokoltsov A, Chen C, Tidwell M, Bauta W, Klugbauer N, Grimm C, Wahl-Schott C, Biel M, Davey R. 2015. Two-pore channels control Ebola virus host cell entry and are drug targets for disease treatment. Science 347 (6225):995-998.

Ventura, C.V., Maia, M., Bravo-Filho, V., Gois, A.L., Belfort, R., Jr., 2016. Zika virus in Brazil and macular atrophy in a child with microcephaly. Lancet 387, 228.

Warren TK, Wells J, Panchal RG, Stuthman KS, Garze NL, Van Tongeren SA, Dong L, Retterer, CJ, Eaton BP, Pegoraro G, Honnold S, Bantia S, Kotian P, Chen X, Taubenheim BR, Welch LS, Minning DM, Babu YS, Sheridan WP, Bavari S. 2014. Protection against filovirus diseases by a novel broad-spectrum nucleoside analogue BCX4430. Nature. 508(7496): p. 402-5.

Wong G. and Kobinger GP. 2015. Backs against the Wall: Novel and Existing Strategies Used during the 2014-2015 Ebola Virus Outbreak. Clin Microbiol Rev 28(3): p. 593-601.

Xia T, Eiteman MA2. 2017, Quercetin Glucoside Production by Engineered *Escherichia coli*.Appl Biochem Biotechnol. Jan. 19, 2017. doi: 10.1007/s12010-017-2403-x.

Zanluca, C., Melo, V.C., Mosimann, A.L., Santos, G.I., Santos, C.N., Luz, K., 2015. First report of autochthonous transmission of Zika virus in Brazil. Mem Inst Oswaldo Cruz 110, 569-572.

\* cited by examiner

FIG. 2D

DMSO 13dbi
Q3G 13dbi
Q3G 7dbi
Q3G 3dbi
Q3G 30min bi
Q3G 1dpi

EBOV

- ● DMSO
- □ 13 dbi
- △ 7 dbi
- ▽ 3 dbi
- ◇ 30 min bi
- ○ 1 dbi post-infection (days)

![Graph showing Weight (% Change) vs Days post Q3G injection for DMSO, 12.5, 25, 50, 100, 200, and 400 mg/kg doses]

FIG. 3C

![Schematic showing EBOV challenge timeline with DMSO 1dbi, Q3G 12.5mg/kg (1dbi), Q3G 25 mg/kg (1dbi), and Q3G 50mg/kg (1dbi) dosing arrows over 0 to 14 days]

FIG. 3F

EBOV

DMSO 1dpi
Q3G 50mg/kg (1dpi)
Q3G 100mg/kg (1dpi)
Q3G 200mg/kg (1dpi)

A: DMSO
B: 50mg/kg
C: 100mg/kg
D: 200mg/kg

000000000000000000
METHODS OF PREVENTING OR TREATING FILOVIRUS AND FLAVIVIRUS DISEASES

CROSS REFERENCE TO RELATED APPLICATIONS

This application claims benefit, under 35 U.S.C. § 119(e), of U.S. provisional application Ser. No. 62/517,562, filed on Jun. 9, 2018. The document above is incorporated herein in its entirety by reference.

STATEMENT REGARDING FEDERALLY SPONSORED RESEARCH OR DEVELOPMENT

N. A.

FIELD OF THE INVENTION

The present invention relates to methods of preventing or treating filovirus and flavivirus diseases. More specifically, the present invention is concerned with methods of preventing or treating filovirus hemorrhagic fevers (e.g., Ebola virus disease and Marburg virus disease) and flavivirus diseases (e.g., Zika virus disease) with a flavonoid, compositions and kits therefore.

REFERENCE TO SEQUENCE LISTING

Pursuant to 37 C.F.R. 1.821(c), a sequence listing is submitted herewith as an ASCII compliant text file named 765-Sequence Listing-12810-668_ST25, that was created on Jun. 1, 2018 and having a size of 2 kilobytes. The content of the aforementioned file named 765-Sequence Listing-12810-668_ST25 is hereby incorporated by reference in its entirety.

BACKGROUND OF THE INVENTION

Filoviruses can cause severe hemorrhagic fevers in humans and non-human primates. Marburgvirus and Ebolavirus are two members of this family that have been identified as causing such fevers. Two large epidemic of Marburg hemorrhagic fevers have been reported in human in 1999 in the Democratic Republic of Congo (DRC) and in Angola in 2005.

Ebola virus disease (EVD) outbreaks occur on more a frequent basis, e.g., in 1995 and 2012 in the DRC, in 2000 and 2008 in Uganda, and the 2014-15 outbreak in West Africa, being the largest ever recorded. It has resulted in over 11 000 deaths in four African countries and highlighting the urgent need for novel therapies to combat this disease. The virus is transmitted to people from wild animals and spreads in the human population through human-to-human transmission. The average EVD case fatality rate is around 50%. Case fatality rates have varied from 25% to 90% in past outbreaks.

There are currently no approved therapies against EBV, although several treatments show promise (reviewed in Wong, 2015).

Small-molecule drugs are of particular interest, due to their comparatively low production costs, potentially non-invasive administration routes, and possibility for cross-protection. To date, numerous small molecules that inhibit Ebola virus in vitro and in vivo have been identified (Warren, 2014; Furuta, 2013; Picazo, 2015).

A few of these compounds have shown protection in animal models of EBOV, which is a critical step for screening potential drug candidates for future human clinical trials (Furuta, 2013; Madelain, 2015; Julander, 2014). Estrogen receptor modulators, clomiphene and toremifene, for example, have been shown to protect 90% and 50% of mice when given 24 h post infection (Johansen, 2013). Similarly, tetrandrine has been found to inhibit Ebola by interacting with NPC1, and protected 80% of mice when given 24 h post infection (Sakurai, 2015). A fourth compound, FGI-106, has demonstrated 100% protection in mice against numerous viruses including Ebola when given 24 h post infection. Additionally, protection at later timepoints has been achieved by GS-5734, nucleoside analogue, (100% protection in mice when given on day 3 post infection) (Warren 2014), and T-705, a broad-spectrum antiviral (100% protection in IFNAR−/− mice when given at 6 days post infection) (Oestereich, 2014).

Although certain candidates are undergoing clinical trials and have had success in promoting recovery from Ebola, to the Applicant's knowledge, these prophylactics and therapeutics have each only been designed and tested against a single species of Ebola, namely one which caused an outbreak. Future outbreaks involving other species would require reformulation and possibly redevelopment. Therefore, a broader spectrum anti-Ebola alternative is highly desirable.

The first reported Zika virus disease (ZVD) outbreak in human occurred in 2007 in the Federal States of Micronesia. The 2015-2016 outbreak of Zika virus disease (ZVD), first reported in Brazil during early 2015 (Zanluca, 2015), has infected millions of people. Zika viruses (ZIKV) infections are associated with fetal microcephaly as well as neurological complications in humans (Cao-Lormeau, 2016; Carteaux, 2016; Mlakar, 2016; Ventura, 2016), the virus can be shed in the semen and vaginal secretions of humans (Mansuy, 2016; Murray, 2017) leading to sexual transmission, and unexpectedly ZIKV infections cause severe damage to the male reproductive organs in male mice (Govero, 2016; Ma, 2016). Vaccines and antivirals, such as monoclonal antibodies (mAbs), are currently in pre-clinical development and not yet approved for use in humans. There are concerns that vaccines and mAb-based products against ZIKV may inadvertently enhance the severity of Dengue virus (DENY) infections (Kawiecki 2016; Richner, 2017), a potentially dangerous undesired side-effect. The development of small molecule drugs is a priority for the control and prevention of ZIKV spread.

The present description refers to a number of documents, the content of which is herein incorporated by reference in their entirety.

SUMMARY OF THE INVENTION

The present invention demonstrated antiviral efficacy of a flavonoid derivative called quercetin-3 β-O-D-glucoside (Q3G) against Ebola and Zika viruses both in vitro and in vivo in small animal models.

In particular, the present invention demonstrated that Q3G not only inhibits the well-studied EBOV, but also a second common ebolavirus isolated from Sudan (SUDV) and the non-human Reston virus (RESTV).

The present invention shows that Q3G has the ability to protect mice from Ebola when given as little as 30 minutes prior to infection. Furthermore, the present invention shows that this compound targets the early steps of viral entry.

The present invention also demonstrated that Q3G inhibits ZIKV infection in vitro, with a half-maximal effective concentration ($EC_{50}$) of between 1.2 to 1.3 µM and a ninety percent effective concentration ($EC_{90}$) of 1.5 µM. Q3G administration daily from 1-8 days post-infection to immunocompromised mice ($Ifnar1^{-/-}$) resulted in protection from ZIKV infection.

More specifically, in accordance with the present invention, there are provided the following items:

1. A method of reducing the risk of filovirus hemorrhagic fever or a symptom thereof in a mammal host exposed to a filovirus, comprising administering an effective amount of quercetin-3 β-O-D-glucoside (Q3G) or an analogue thereof, or a composition comprising Q3G or analogue thereof and a pharmaceutically acceptable carrier, to said host prior to said exposure.

2. The method of item 1, wherein the filovirus hemorrhagic fever or symptom thereof is Ebola virus disease (EVD) or a symptom thereof and the filovirus is an ebolavirus.

3. The method of item 1, wherein the host is infected by the Zaire ebolavirus (EBOV).

4. The method of item 1, wherein the host is infected by the Sudan ebolavirus (SUDV).

5. The method of item 1, wherein the host is infected by the Reston ebolavirus (RESTV).

6. The method of item 1, wherein Q3G, the analogue thereof or the composition is administered to the host every other day beginning 13 days or less prior to said exposure and until 11 days after exposure.

7. The method of item 1, wherein Q3G, the analogue thereof or the composition is administered to the host every other day beginning 7 days or less prior to said exposure and until 11 days after exposure.

8. The method of item 1, wherein the Q3G, the analogue thereof or the composition is administered to the host every other day beginning 3 days or less prior to said exposure and until 11 days after exposure.

9. The method of item 1, wherein Q3G, the analogue thereof or the composition is administered to the host every other day beginning 1 days or less prior to said exposure and until 11 days after exposure.

10. The method of item 1, wherein Q3G, the analogue thereof or the composition is administered to the host every other day beginning 30 minutes or less prior to said exposure and until 11 days after exposure.

11. The method of item 1, wherein the effective amount of Q3G or the analogue thereof is between about 0.8 mg/kg to 20 mg/kg, 0.8 mg/kg to 10 mg/kg, or 0.8 mg/kg to 8 mg/kg daily.

12. A method of preventing or treating a Zika virus disease (ZVD) or a symptom thereof in a mammal host exposed to a Zika virus, comprising administering an effective amount of quercetin-3 β-O-D-glucoside (Q3G) or an analogue thereof, or a composition comprising Q3G or the analogue thereof and a pharmaceutically acceptable carrier, to said host after said exposure.

13. The method of item 12, wherein Q3G, the analogue thereof or the composition is administered to the host every day for seven days beginning 1 day after said exposure.

14. The method of item 1, wherein the host is a human host.

15. The method of item 1, wherein Q3G, the analogue thereof or the composition is administered by an oral route.

16. The method of item 1, wherein Q3G, the analogue thereof or the composition is administered by a parenteral route.

17. The method of item 1, wherein Q3G is administered.

18. A kit for use in the prevention or treatment of a filovirus hemorrhagic disease or a flavivirus disease comprising (i) quercetin-3 β-O-D-glucoside (Q3G) or an analogue thereof, or a composition comprising Q3G or the analogue thereof and a pharmaceutically acceptable carrier; and (ii) (a) another antiviral agent; (iii) instructions to use (i) in the prevention or treatment of a filovirus hemorrhagic disease or a flavivirus disease; or (c) a combination of (a) and (b).

19. The kit of item 18, comprising between 11 and 25 daily doses of 30 mg to 2 g, or 30 mg to 1 mg, or 30 mg to 800 mg of Q3G or the analogue thereof.

20. The kit of item 18, wherein (i) is Q3G.

21. A composition comprising (i) quercetin-3 β-O-D-glucoside (Q3G) or an analogue thereof; and (ii) (a) another antiviral agent; (b) a pharmaceutically acceptable carrier; or (c) a combination of (a) and (b).

22. The composition of item 21, wherein (i) is Q3G.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

(FIG. 1A) Chemical structure of Q3G. (FIG. 1B) VeroE6 cells were pre-treated with 10 µM Q3G for one hour and then infected with EBOV-Kikwit-GFP (MOI=0.1) at 37° C. and incubated for 72 h in the presence of 10 NM Q3G. (FIG. 1C) The $EC_{50}$ of Q3G was determined against EBOV-Kikwit-GFP by pre-treating VeroE6 cells with serial dilutions of Q3G for 1 hour and then infecting them with virus (MOI=0.1) at 37° C. hour for 72 h in the presence of Q3G at which time the fluorescence was quantified. (FIG. 1D) To determine cell viability following Q3G treatment VeroE6 cells were treated with serial dilutions of Q3G. Viability was measured after 72 hours by a resazurin dye-based assay and data was normalized to untreated controls. (FIG. 1E) Inhibition of EBOV-Makona and SUDV viruses was determined by pre-treating cells with 10 µM Q3G for one hour and then infecting them with virus (MOI=0.1) at 37° C. for 1 hour. Cells were collected and the amount of viral RNA was quantified at 5 days post-infection by RT-qPCR (Ct value=threshold cycle value i.e. number of cycles needed to detect real signal in sample). (FIG. 1F) Inhibition of EBOV-Makona and SUDV viruses was determined by pre-treating cells with 10 µM Q3G for one hour and then infecting them with virus (MOI=0.1) at 37° C. for 1 hour. Cells were collected and the amount of viral RNA was quantified at 5 days post-infection using a 50% Tissue culture Infective Dose ($TCID_{50}$) assay. All experiments were performed in triplicate and error bars represent the standard error of the mean. ***=p-value <0.001.

FIGS. 2A-H: Prophylactic treatment with Q3G promotes survival and inhibits Ebola virus replication. (FIG. 2A) Experimental plan outlining treatment. Six-to-eight-week-old female C57BL/6 mice (Charles River) were treated with 50 mg/kg of Q3G (n=10) or 10% DMSO (n=10) via intraperitoneal injection every other day from day −14 to day 12. Mice in both groups received a challenge dose of 1000× $LD_{50}$ of mouse-adapted Ebola virus (Mayinga isolate) in 200 µl of PBS (pH 7.4) by intraperitoneal injection on day 0. (FIG. 2B) Survival and (FIG. 2C) changes in weight of Q3G treated and untreated mice. (FIG. 2D) Experimental plan outlining treatment. Six-to-eight-week-old female C57BL/6 mice were treated with 50 mg/kg of Q3G (n=10 per group)

or 10% DMSO (n=10) via intraperitoneal injection either every other day from day −13 to day 11 (13 dbi); every other day from day −7 to day 11 (7 dbi); every other day from day −3 to day 10 (3 dbi); every other day from −30 min to day 11 (30 min bi); or every other day from day 1 to day 11 (1 dbi). Mice in all six groups received a challenge dose of 1000×LD$_{50}$ of mouse-adapted Ebola virus (Mayinga isolate) in 200 μl of PBS (pH 7.4) by intraperitoneal injection on day 0. (FIG. 2E) Survival and (FIG. 2F) changes in weight of Q3G treated and untreated mice. (FIG. 2G) Experimental plan outlining treatment. Six-to-eight-week-old female Balb/c mice were treated with 50 mg/kg of Q3G (n=10) or 10% DMSO (n=10) via intraperitoneal injection every other day beginning from day −1 until day 5. Mice in both groups received a challenge dose of 1000×LD$_{50}$ of mouse-adapted Ebola virus (Mayinga isolate) in 200 μl of PBS (pH 7.4) by intraperitoneal injection on day 0. (FIG. 2H) Virus in the blood, liver, kidney, spleen, lung and brain was quantified by qRT-PCR amplification of the Ebola L gene in Q3G treated and untreated mice on Day 6. All experiments were performed in triplicate and error bars represent the standard error of the mean. ***=p-value <0.001.

FIGS. 3A-H: Dosing and toxicity of Q3G. Naive C57BL/6 male mice were dosed with 12.5-400 mg/ml Q3G or 10% DMSO intraperitoneally. (FIG. 3A) Survival and (FIG. 3B) changes in body weight were monitored for 14 days as an indication of toxicity. Arrows point to lines or curves of interest; brackets bundle indistinguishable lines or curves. (FIG. 3C) Experimental plan outlining treatment. Six-to-eight-week-old female Balb/c mice were treated with 12.5 mg/kg (1 dbi), 25 mg/kg (1 dbi), or 50 mg/kg (1 dbi) Q3G (n=10 per group) or 10% DMSO (n=10) via intraperitoneal injection every other day beginning from day −1 until day 11. Mice in all groups received a challenge dose of 1000×LD$_{50}$ of mouse-adapted Ebola virus (Mayinga isolate) in 200 μl PBS (pH 7.4) by intraperitoneal injection on day 0. (FIG. 3D) Survival and (FIG. 3E) changes in weight of Q3G treated and untreated mice. (FIG. 3F) Experimental plan outlining treatment. Six-to-eight-week-old female Balb/c mice received a challenge dose of 1000×LD$_{50}$ of mouse-adapted Ebola virus (Mayinga isolate) in 200 μl of PBS (pH 7.4) by intraperitoneal injection on day 0. Starting at 24 hours post infection, mice were treated with 50 mg/kg, 100 mg/kg or 200 mg/kg of Q3G (n=10) or 10% DMSO (n=10) every other day via intraperitoneal injection until day 11. (FIG. 3G) Survival and (FIG. 3H) changes in weight of Q3G treated and untreated mice.

FIGS. 4A-C: Impact of Q3G on ebolaviruses entry and infectivity. (FIG. 4A) VeroE6 cells were pre-treated with 10 μM Q3G for one hour and then infected with VSV-EBOV, VSV-SUDV or VSV-RESTV (MOI=0.1) at 37° C. for 1 hour in the absence of Q3G. (FIG. 4B) VeroE6 cells were pre-treated with 10 μM Q3G for one hour and then infected with VSV-EBOV, VSV-SUDV or VSV-RESTV (MOI=0.1) at 37° C. for 1 hour in the presence of Q3G. (FIG. 4C) 200 ul of VSV, VSV-EBOV, VSV-SUDV and VSV-RESTV virus stocks were incubated with 10 μM Q3G for 1 h at 37° C. and then titered using a TCID$_{50}$ assay. Fresh media was added without Q3G and supernatants were harvested at 72 h and titered using a TCID$_{50}$ assay. All experiments were performed in triplicate and error bars represent the standard error of the mean. ***=p-value <0.001.

(FIG. 9A) Post-exposure treatment schedule of Q3G or PBS. (FIG. 9B) Survival and (FIG. 9C) weight loss over time. Mice were challenged intraperitoneally with 1×106 PFU of the PRVABC59 isolate.

DESCRIPTION OF ILLUSTRATIVE EMBODIMENTS

The present invention provides a method of preventing or treating a filovirus hemorrhagic fever or any symptom thereof comprising administering Quercetin-3-β-O-D-glucoside (Q3G) (also called isoquercetin, quercetin-3-glucoside, quercetin-3-O-glucoside, Quercetin-3-D-glucoside) or an analogue to a subject in need thereof. As used herein analogues of Q3G includes other quercetin glycosides such as enzymatically modified isoquercitrin (EMIQ), a polyglycosylated Q3G analogue, rutinoside, or rutoside (also called rutine or sophorine).

The present invention also provides a method of preventing or treating Zika fever (or Zika virus disease (ZVD) or Zika) or any symptom thereof comprising administering Q3G to a subject in need thereof.

Figure 1A:
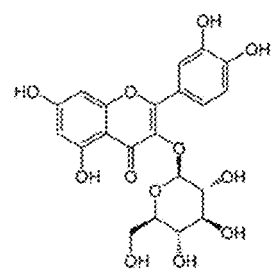
FIGS. 1A-F: Q3G inhibits replication of Ebola virus in vitro.

Q3G has a molecular weight of 464.38 is a natural derivative of quercetin containing a glucoside molecule (FIG. 1A). It is a flavonoid naturally found in various plants (e.g., *Mangifera indica* (mango), *Rheum nobile* (the Noble rhubarb), leaves of *Annona squamosa*, leaves of *Camellia sinensis* (tea), *Carpobrotus edulis*, Ashanti pepper seed, *Morus nigra* L. Leaves, *Chrysanthemum balsamita* var. *balsamita*, *Mangifera indica* Leaves, *Hypericum japonicum* Thunb, *Lycium barbarum* L. etc.) and as such present in foods and drinks. It can also be made recombinantly in microorganisms (e.g., in *E. coli* (see Xia, 2017).

Diseases

Filovirus hemorrhagic fevers are caused by viruses of the filoviridae family. This family includes the Ebola virus and the Marburg virus. Symptoms of a filovirus hemorrhagic fever includes the presence of viral antibodies or RNA in blood, low white blood cell, low platelet counts, elevated liver enzymes, tiredness, weakness, decreased appetite, fever (usually higher than 38.3° C.), sore throat, flushing of the face and chest, rash, small red or purple spots (petechiae), bleeding, swelling caused by edema, low blood pressure (hypotension), shock, decreased function of the liver and kidneys, weight loss, decreased blood clotting, internal bleeding, external bleeding (e.g., from mucous membranes or sites of needle punctures), low blood pressure, "VHF syndrome" (capillary leak, bleeding diathesis, and circulatory compromise leading to shock). It may also include muscle pain, headache, vomiting, and diarrhea. The severity of symptoms varies with the type of virus. The signs and symptoms typically start between two days and 21 days after contracting the virus, sometimes longer than 21 days, and usually between 4 to 10 days. The virus spreads by direct contact with body fluids such as blood, semen and breast milk with an infected animal such as a human from or with an object contaminated with such bodily fluid. Confirmation that symptoms are caused by viral infection is made using the following diagnostic methods: antibody-capture enzyme-linked immunosorbent assay (ELISA); antigen-capture detection tests; serum neutralization test; reverse transcriptase polymerase chain reaction (RT-PCR) assay; electron microscopy; virus isolation by cell culture. For ZVD, expression of ZIKV nonstructural protein 1 (NS1) can be used. NS1 is known to be a major host-interaction molecule that plays a role in virus replication, pathogenesis and immune evasion (Rastogi, 2016).

In a specific embodiment, the present invention provides a method for preventing or treating an Ebola virus disease (EVD) or any symptom thereof or a Marburg virus disease (MVD) in a subject in need thereof.

The EVD is caused by viruses of the genus ebolavirus, a virological taxon. The five known ebolavirus species are Bundibugyo ebolavirus (BDBV), Reston ebolavirus (RESTV), Sudan ebolavirus (SUDV), Taï Forest ebolavirus (TAFV) (originally Côte d'Ivoire ebolavirus), and Zaire ebolavirus (EBOV). BDBV, SUDV, TAFV and EBOV cause EVD in humans, while RESTV causes EBV in other primates.

The MVD may be caused by the Marburg virus (MARV) and the Ravn virus (RAW).

In a specific embodiment, the present invention provides a method for preventing or treating a flavivirus disease or any symptom thereof in a subject in need thereof. In a specific embodiment, the flavivirus is a Zika virus.

The ZVD often causes no or only mild symptoms in adults. The symptoms may include fever, red eyes, headache, vomiting, muscle and joint pains, a characteristic maculopapular skin rash and may result in Guillain-Barré syndrome. Symptoms generally last less than 7 days. The infection can also spread from a pregnant woman to her baby and result in microcephaly, severe brain malformations, and other birth defects. A blood, urine, semen or saliva assay to detect the presence of the Zika virus RNA can confirm Zika infection As used herein, the term "exposure" refers to entry in contaminated or at-risk territories, and/or contact with contaminated or at-risk humans, animals, insects or objects. As used herein, the terms "at-risk territories" refer to territories (e.g., countries) where there are confirmed (e.g., serological evidence) or probable cases of the subject infection (e.g., filovirus or Zika virus infection), or where cases of the subject infection have been reported in the past. At-risk individuals refer to individual that have been diagnosed with or suspected of having the subject infection (e.g., filovirus or Zika virus infection) or individual that have been in contact directly or indirectly with individuals that have been diagnosed with or suspected or having a subject infection, or have been in an at-risk territory in the last two months, or in the last 3 weeks. Without being so limited, these individuals include health-care workers taking care of infected individuals, and laboratory personal working with samples from infected hosts. At-risk objects are objects that have been manipulated by at-risk individuals or present in an at-risk territory. At-risk animals refer to any animal that can be a host (naturally or not) for a subject infection. As used herein "contact with an at-risk individual" includes sexual activity, and direct contact (through broken skin or mucous membranes) with the blood, secretions, organs or other bodily fluids of infected people or direct contact with the body of the deceased. As used herein "contact with an at-risk object" includes direct contact (through broken skin or mucous membranes) with a surface or material (e.g., bedding, clothing) contaminated with these fluids and blood transfusion.

With reference to filovirus infections, and without being so limited, at-risk territories refer to tropical rainforests; Africa including Democratic Republic of the Congo, Guinea, Liberia, Sierra Leone, Angola, Zimbabwe, Nigeria, and Senegal. At-risk animals include fruit bats of the Pteropodidae family, chimpanzees, gorillas, monkeys, forest antelope and porcupines living in at-risk territories.

With reference to Zika virus infections, and without being so limited, at-risk territories include countries of the Central and South America including Brazil, Colombia, Ecuador and El Salvador; the Caribbean including the Dominican Republic, Puerto Rico, and Jamaica; the equatorial belt from Africa to Asia; the Federal States of Micronesia; Yap Island; French Polynesia; Uganda; etc. At-risk animals and insects include mosquitoes such as daytime-active *Aedes* mosquitoes, such as *A. aegypti, A. albopictus,* Ae. *africanus,* Ae. *apicoargenteus,* Ae. *luteocephalus,* Ae. *Albopictus,* Ae. *Vittatus,* Ae. *furcifer. Aedes hensilli* and *Aedes polynesiensis,* west African monkeys and rodents.

As used herein the terms "treat/treating/treatment" and "prevent/preventing/prevention" as used herein, refers to eliciting the desired biological response, i.e., a therapeutic and prophylactic effect, respectively. In accordance with the subject invention, the therapeutic effect comprises one or more of a decrease/reduction in the severity of a human disease (e.g., a reduction or inhibition of a filovirus hemorrhagic fever (e.g., EVD, MVD) or Zika virus disease, or symptom thereof), a decrease/reduction in at least one symptom or disease-related effect, an amelioration of at least one symptom or disease-related effect, and an increased survival time of the affected host animal, following administration of Q3G, or an analogue thereof, or of a composition comprising Q3G, or an analogue thereof. In accordance with the invention, a prophylactic effect may comprise a complete or partial avoidance/inhibition of filovirus hemorrhagic fever (e.g., EVD, MVD) or ZVD, or a symptom thereof or a delay of filovirus hemorrhagic fever (e.g., EVD, MVD) or ZVD, or a symptom thereof (e.g., a complete or partial avoidance/inhibition of hemorrhage or a delay of hemorrhage development), and an increased survival time of the affected host animal, following administration of Q3G, or an analogue thereof or of a composition comprising Q3G, or an analogue thereof.

As such, a "therapeutically effective" or "prophylactically effective" amount of Q3G, or an analogue thereof or of a composition comprising Q3G, or an analogue thereof, may be administered to a subject in need thereof, in the context of the methods of treatment and prevention, respectively, described herein.

As used herein the term "subject" or "host" or "patient" is meant to refer to any animal, such as a mammal including human, primates (e.g., monkey, gorilla), pets such as mice, rat, dog, cat, pig, cow, horse, etc. In a particular embodiment, it refers to a human.

A "subject in need thereof" or a "patient" or "host in need thereof" in the context of the present invention is intended to include any subject that will benefit or that is likely to benefit from the prevention and/or treatment of an hemorrhagic fever (e.g., EVD, MVD) or flavivirus disease (e.g., ZVD). In an embodiment, the subject in need thereof is a subject diagnosed with an hemorrhagic fever (e.g., EVD, MVD) or flavivirus disease (e.g., ZVD). In another embodiment, the subject in need thereof is a human that intends to travel or live in an at-risk territory or be in contact with at least one of an at-risk individual, at-risk animal, at-risk insect or at-risk object. In a specific embodiment, it refers to a health care or laboratory professional that is likely to become in contact with at least one of an at-risk individual, at-risk animal, at-risk insect or at-risk object.

As used herein, the term "a" or "the" means "at least one".

Although the present invention has been described hereinabove by way of specific embodiments thereof, it can be modified, without departing from the spirit and nature of the subject invention as defined in the appended claims.

Compositions

The present invention also relates to pharmaceutical compositions comprising Q3G or an analogue thereof.

Without being so limited, the medicaments/pharmaceutical compositions of the invention may be administered orally, for example in the form of tablets, coated tablets, dragees, hard or soft gelatin capsules, solutions, emulsions or suspensions. Administration can also be carried out rectally, for example using suppositories; locally, topically, or percutaneously, for example using ointments, creams, gels or solutions; or parenterally, e.g., intravenously, intramuscularly, intraperitoneal, intradermal, subcutaneously, intrathecally or transdermally, using for example injectable solutions. Furthermore, administration can be carried out sublingually, nasally, as ophthalmological preparations or as an aerosol, for example in the form of a spray, such as a nasal spray.

For the preparation of tablets, coated tablets, dragees or hard gelatin capsules, the compounds of the present invention may be admixed with any known pharmaceutically inert, inorganic or organic excipient and/or carrier. Examples of suitable excipients/carriers include lactose, maize starch or derivatives thereof, talc or stearic acid or salts thereof.

Suitable excipients for use with soft gelatin capsules include for example vegetable oils, waxes, fats, semi-solid or liquid polyols etc. According to the nature of the active ingredients it may however be the case that no excipient is needed at all for soft gelatin capsules.

For the preparation of solutions and syrups, excipients which may be used include for example water, polyols, saccharose, invert sugar and glucose.

For injectable solutions, excipients which may be used include for example water, saline, alcohols, polyols, glycerin, vegetable oils and other appropriate excipients.

For suppositories, and local or percutaneous application, excipients which may be used include for example natural or hardened oils, waxes, fats and semi-solid or liquid polyols.

The medicaments/pharmaceutical compositions may also contain preserving agents, solubilizing agents, stabilizing agents, wetting agents, emulsifiers, sweeteners, colorants, odorants, salts for the variation of osmotic pressure, buffers, coating agents and/or antioxidants. They may also contain other therapeutically active agents.

Intravenous, or oral administrations are preferred forms of use. The dosages in which Q3G or an analogue thereof are administered in effective amounts depend on the nature of the specific active ingredient, the age and the requirements of the subject and the mode of application.

As mentioned above, the pharmaceutical compositions of the invention can contain a pharmaceutically acceptable carrier including, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. Pharmaceutically acceptable carriers also can include physiologically acceptable aqueous vehicles (e.g., physiological saline) or other known carriers appropriate to specific routes of administration.

Q3G or an analogue thereof may be incorporated into dosage forms in conjunction with any of the vehicles which are commonly employed in pharmaceutical preparations, e.g., talc, gum arabic, lactose, starch, magnesium stearate, cocoa butter, aqueous or non-aqueous solvents, oils, paraffin derivatives or glycols. Emulsions such as those described in U.S. Pat. No. 5,434,183, incorporated herein by reference, may also be used in which vegetable oil (e.g., soybean oil or safflower oil), emulsifying agent (e.g., egg yolk phospholipid) and water are combined with glycerol. Methods for preparing appropriate formulations are well known in the art (see e.g., Remington's Pharmaceutical Sciences, 16th Ed., 1980, A. Oslo Ed., Easton, Pa. incorporated herein by reference).

In cases where parenteral administration is elected as the route of administration, preparations containing Q3G or an analogue thereof may be provided to subjects in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles may include fluid and nutrient replenishers, electrolyte replenishers, such as those based upon Ringer's dextrose, and the like.

It is a prerequisite that all excipients used in the manufacture of the compositions of the present invention, such as carriers, are non-toxic and more generally pharmaceutically acceptable.

As used herein, "pharmaceutically acceptable" such as pharmaceutically acceptable carrier, excipient, etc., means pharmacologically acceptable and substantially non-toxic to the subject to which Q3G or an analogue thereof is administered.

Any amount of a pharmaceutical composition can be administered to a subject. The dosages will depend on many factors including the mode of administration. Typically, the amount of Q3G or an analogue thereof contained within a single dose will be an amount that effectively prevent, delay or treat the disease or condition to be treated, delayed or prevented without inducing significant toxicity.

The effective amount of Q3G or an analogue thereof may also be measured directly. The effective amount may be given daily or weekly or fractions thereof. Typically, a pharmaceutical composition of the invention can be administered in an amount from about 0.8 mg/kg to about 10 mg/kg (0.8 mg/kg to 8 mg/kg), In another specific embodiment, it refers to up to about 14.3 mg per kg of body weight per day (e.g., 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.5 mg, 6 mg, 6.5 mg, 7 mg, 7.5 mg, 8 mg, 8.5 mg, 9 mg, 9.5 mg, 10 mg, or 20 mg) per kg of body weight per day. Dosages may be provided in either a single or multiple dosage regimen. For example, in some embodiments, for a human of about 40 kg to about 100 kg, the effective amount may range from about 30 mg to about 1 gram of the composition per day, 32 mg to about 800 mg of the composition per day about 500 mg to about 7 grams of the composition per week, about 500 mg to about 6 grams of the composition per week, about 560 mg to about 5.6 grams of the composition per week, about 50 mg to about 2 grams of the composition every other day, about 60 mg to about 1600 grams of the composition every other day, about 64 mg to about 1600 grams of the composition every other day. In a more specific embodiment, it refers, for a human of 40-100 kg, to an amount of 30 mg to 910 g daily (e.g., 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 450 mg, 460 mg, 470 mg, 480 mg, 490 mg, 500 mg, 510 mg, 520 mg, 530 mg, 540 mg, 550 mg, 560 mg, 570 mg, 580 mg, 590 mg, 600 mg, 610 mg, 620 mg, 730 mg, 740 mg, 750 mg, 760 mg, 770 mg, 780 mg, 790 mg, 800 mg, 810 mg, 820 mg, 830 mg, 840 mg, 850 mg, 860 mg, 870 mg, 880 mg, 890 mg, 800 mg, or 810 mg, daily). In another specific embodiment, it refers to an amount 1000 to 2300 mg daily for a human subject of about 70 kg. In another specific embodiment, it refers to about 12.5 to 50 mg/kg daily. The Q3G may be administered once every two days, once a day, twice or three times daily, twice a week, or three times a week, or at least once every 2, 3, 4, 5, or 6 days, for at least 1-18 weeks, or for at least 2-16 weeks, or for at least 1, 3, 4, 5, 6, 7, 8, 9, 10, 11, 12, 13, 14, 15 weeks. As a comparison, daily recommended doses of Q3G used as a food supplement are of about 1136 to 2272 mg per day (i.e. about 12.5 to 50 mg/kg per day).

In specific embodiments (e.g., in a prophylactic treatment against a filovirus hemorrhagic fever (e.g., Ebola virus infection)), the Q3G or its analogue is administered at least 2 weeks, or 13 days, 12 days, 11 days, 10 days, 9 days, 8 days, 7 days, 6 days, 5 days, 4 days, 3 days, 2 days, 1 day, 20 hours, 15 hours, 10 hours, 9 hours, 8 hours, 7 hours, 6 hours, 5 hours, 4 hours, 3 hours, 2 hours, 1 hour, 45 minutes, 30 minutes, 20 minutes, 15 minutes, 10 minutes, or 5 minutes prior to exposure. In a specific embodiment, it is administered between 3 days and 30 minutes before exposure. Administration of Q3G or its analogue may be continued at least 1 day, 2 days, 3 days, 4 days, 5 days, 6 days, 7 days, 8 days, 9 days, 10 days, 11 days, 12 days or more after exposure. In other specific embodiments (e.g., in a therapeutic treatment against a filovirus hemorrhagic fever (e.g., Ebola virus infection) or against a flavivirus infection (e.g., Zika virus infection)), the Q3G is administered 10 minutes, 20 minutes, 30 minutes, 40 minutes, 50 minutes, 1 hour, 2 hours, 3 hours, 4 hours, 5 hours, 6 hours, 7 hours, 8 hours, 9 hours, 10 hours, 11 hours, 12 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 8 days, 9 days, 10 days or more after treatment. In a specific embodiment, it is administered before the end of the incubation period. In a specific embodiment, it is administered less than 21 days after exposure. In another specific embodiment, it is administered less than 10 days after exposure. In another specific embodiment against a flavivirus infection (e.g., Zika virus infection), it is administered less than 4 days after exposure. In another specific embodiment, (e.g., in a treatment against a flavivirus infection (e.g., Zika virus infection)), the Q3G or its analogue is administered 1 day after treatment and continued daily for 6 days.

These are simply guidelines since the actual dose must be carefully selected and titrated by the attending physician based upon clinical factors unique to each patient. The optimal daily dose will be determined by methods known in the art and will be influenced by factors such as the age of the patient and other clinically relevant factors. In addition, patients may be taking medications for other diseases or conditions. The other medications may be continued during the time that the pharmaceutical composition of the invention is given to the patient, but it is particularly advisable in such cases to begin with low doses to determine if adverse side effects are experienced. Possible deleterious interactions have been reported with certain drugs and such combination should be avoided (e.g., Aspirin™, Coumadin, cyclosporine etc.).

Combinations

In accordance with another aspect, there is provided a combination of Q3G or an analogue thereof with another antiviral inhibitor or therapy against an hemorrhagic fever or flavivirus disease (e.g., Anti-filovirus (e.g., anti-Ebola, or Anti-Marburg virus) or anti-flavivirus (e.g., anti-Zika virus)) and/or with a non-pharmaceutical treatment/regimen such as for flavivirus infection, use of insect repellent containing DEET, picaridin, or oil of lemon eucalyptus (OLE). Without being so limited, such an antiviral inhibitor or therapy against an hemorrhagic fever or flavivirus disease include ribavirin, lamivudine (against filovirus), vaccine as well as generally supportive therapy that replenishes intravenous fluids, maintains blood pressure, and other bodily functions that are administered to mammals (e.g., human beings) infected with hemorrhagic fevers.

In accordance with an aspect, there is provided a composition comprising Q3G or an analogue thereof, and (i) another antiviral agent; (ii) a pharmaceutically acceptable carrier; or (iii) a combination of (i) and (ii). In accordance with another aspect, there is provided a method for preventing or treating a filovirus hemorrhagic fever or a flavivirus disease or a symptom thereof comprising administering an effective amount of Q3G or an analogue thereof; and (i) another antiviral agent; and/or (ii) a non-pharmaceutical means.

In a specific embodiment, said composition is a pharmaceutical composition. In another specific embodiment, the composition comprises (i) Q3G or an analogue thereof; and (ii) another antiviral agent.

Kits

In accordance with another aspect of the present invention, there is provided a kit comprising Q3G or an analogue thereof or the above-mentioned composition, and instructions to use same in the prevention or treatment of an hemorrhagic fever (e.g., EVD, MVD) or flavivirus disease (e.g., ZVD) or of a symptom thereof.

In a specific embodiment of the kit, the kit further comprises: (i) another antiviral agent; (iii) instructions to use same in the prevention or treatment of an hemorrhagic fever (e.g., EVD, MVD) or flavivirus disease (e.g., ZVD) or of a symptom thereof; or (iii) a combination of (i) and (ii).

The present invention is illustrated in further details by the following non-limiting examples.

Example 1: Material and Methods

Molecules

Q3G was obtained commercially (Sigma-Aldrich, 17793).

Cells and Viruses

Vero E6 cells were maintained in Dulbecco's Modified Eagle Medium (HyClone) (DMEM) supplemented with 10% fetal bovine serum (Sigma-Aldrich). The generation of pseudotyped vesicular stomatitis viruses containing the glycoproteins of Ebola virus, Sudan virus and Reston virus (VSVΔGP-EBOV, VSVΔGP-SUDV, VSVΔGP-RSTV) has been published previously (Qiu, 2011; Cote, 2004). The following ebolaviruses were used: EBOV-Kikwit-GFP (based on *H. sapiens*-tc/COD/1995/Kikwit-9510621, Genbank accession no. AY354458), EBOV-Makona (*H. sapiens*-tc/GIN/2014/Gueckedou-007, Genbank no. KJ660347.2), SUDV-Boniface (*H. sapiens*-tc/SUD/1976/Boniface, Genbank accession no. FJ968794.1), and mouse-adapted EBOV (Ebola virus USAMRIID/BALB/c-lab/COD/1976/Mayinga-MA-p3).

Two different ZIKV strains from the Asian lineage, which were isolated from laboratory-confirmed patients, were used: PLCal_ZV (GenBank KF993678.1) for the in vitro experiments, and PRVABC59 (GenBank KU501215) for the in vivo experiments. Stock viruses were grown in Vero cells (ATCC, CCL-81), and stored at −80° C.

Virus Infections in BSL-4

All work with Ebola infectious virus was performed in the Biosafety Level 4 (BSL-4) facility at the National Microbiology Laboratory (NML) of the Public Health Agency of Canada (PHAC) in the Canadian Science Centre for Human and Animal Health (CSCHAH; Winnipeg, Canada). All experiments with Zika viruses were conducted in the Biosafety Level 2 (BSL-2) facility at the NML. All procedures were conducted in accordance with international protocols appropriate for these levels of biosafety.

All animal work was performed in accordance with guidelines laid out by the Canadian Council on Animal Care (CCAC), and protocols were approved by Applicant's Animal Care Committee.

Cell Viability Assays

The toxicity of Q3G was evaluated in Vero E6 cells by using the PrestoBlue™ Cell Viability Reagent, which is a resazurin dye-based assay (Life Technologies, Canada). Cells were plated and allowed to adhere overnight and then treated with various concentrations of Q3G for 2 hours. Control cells received an equivalent volume of 10% DMSO only. PrestoBlue™ Cell Viability Reagent was added according to the manufacturer's protocol. Viability was determined by comparing fluorescence readings of treated cells to untreated controls. All samples were run in triplicate, and each experiment was performed a minimum of three times. The $CC_{50}$ and $CC_{90}$ values were calculated using a four-parameter logistic regression in Prism5™ (GraphPad).

Q3G Dose Response Curve and $IC_{50}$ Calculation

Vero E6 cells were pre-treated with Q3G (0-200 μM) or DMSO for 1 hour at 37° C. and infected with an MOI=0.1 of eGFP-expressing EBOV in the presence of Q3G or DMSO for 1 hour at 37° C. The inoculum was removed and replaced with fresh medium (DMEM 2% FBS). Cells were then further incubated for 72 h in the presence of Q3G or DMSO. At 72 h, the cells were imaged using an EVOS FL and fixed with 10% formalin for 48 hrs, the green fluorescent protein signal was quantified on a Biotek Synergy™ HTX plate reader. Infection was determined by comparing fluorescence readings of Q3G-treated infected cells to DMSO-treated controls. The $EC_{50}$, and $EC_{90}$, values were calculated using a four-parameter logistic regression in Prism5™ (GraphPad). Selectivity index values were calculated as $CC_{50}/EC_{50}$.

Quantification of EBOV and SUDV by qPCR for In Vitro Studies

Vero E6 cells were first treated with 10 μM Q3G for 1 hour prior to infection. Cells were then infected with an MOI=0.1 of EBOV-Makona or SUDV for 1 hour at 37° C. in the presence of Q3G. Cells were then washed with PBS and media was replaced with DMEM supplemented with 1% penicillin/streptomycin, 4% fetal bovine serum and Q3G. At 5 days post infection cell supernatant was placed in AVL™ buffer (Qiagen) and viral RNA was extracted using the QIAamp™ viral RNA mini kit (Qiagen). EBOV and SUDV genomic material was detected using the LightCycler™ 480 RNA Master Hydrolysis Probes (Roche) kit, targeting the RNA polymerase gene (nucleotides 16472 to 16538, AF086833). PCR conditions were as follows: 63° C. for 3 minutes, 95° C. for 30 seconds, and cycling of 95° C. for 15 seconds, 60° C. for 30 seconds for 45 cycles on the ABI StepOnePlus™ Thermocycler. The lower detection limit for this assay is 86 genome equivalents (GEQ)/mL. The sequences of primers used were as follows: EBOV-L-F2 (CAGCCAGCAATTTCTTCCAT) (SEQ ID NO: 1), EBOV-L-R2 (TTTCGGTTGCTGTTTCTGTG) (SEQ ID NO: 2), EBOV-L-P2FAM (FAM-ATCATTGGCGTACTGGAGGAGCAG-BHQ1) (SEQ ID NO: 3), SEBOV-L-F (CAGAAGACAATGCAGCCAGA) (SEQ ID NO: 4), SEBOV-L-R (TTGAGGAATATCCCACAGGC) (SEQ ID NO: 5) and SEBOV-L-PFAM (CTGCTAGCTTGGCCAAAGTCACAAG-BHQ1) (SEQ ID NO: 6).

$TCID_{50}$ Assay

Determination of the amount of virus that produces cytopathic effects in 50% of cells in culture.

Quantification of EBOV by qPCR for In Vivo Studies

RNA was extracted from whole blood samples with the QIAamp™ viral RNA mini kit (Qiagen) and from spleen, kidney, lung, brain and liver tissue samples using the RNeasy™ Plus mini kit (Qiagen). EBOV genomic material was detected as described above.

In Vivo Treatment (Prophylactic and Therapeutic) with Q3G and Ebola

Six-to-eight-week-old female Balb/c or C57BL/6 mice (Charles River) were treated with 12.5 mg/kg, 25 mg/kg, or 50 mg/kg of body weight of Q3G or 10% DMSO at the time points indicated. Q3G was administered by intraperitoneal injection. Q3G was administered every other day starting either 14 days, 13 days, 7 days, 3 days, 1 day or 30 minutes pre-challenge, or 24 h/1 day post-challenge. Mice in all groups received a challenge dose of 1000×$LD_{50}$ of mouse-adapted Ebola virus (Mayinga variant) in 200 μl of DMEM (pH 7.4) by intraperitoneal injection. Following infection, the treatment regimen continued at the same dosage for a various number of days (see FIG. 2A (continued for 12 days), 2D (continued for 10 or 11 days), 2G (continued for 5 days) and 3C and 3F (continued for 11 days).

In Vivo Treatment with Q3G and Zika

In vivo therapeutic effects of Q3G in immunocompromised mice lacking the receptor for type I interferon (Jackson laboratories, 32045-JAX), hereafter referred to as Ifnar1$^{-/-}$, was also evaluated.

Dosing and Toxicity Study

Figure 3A:
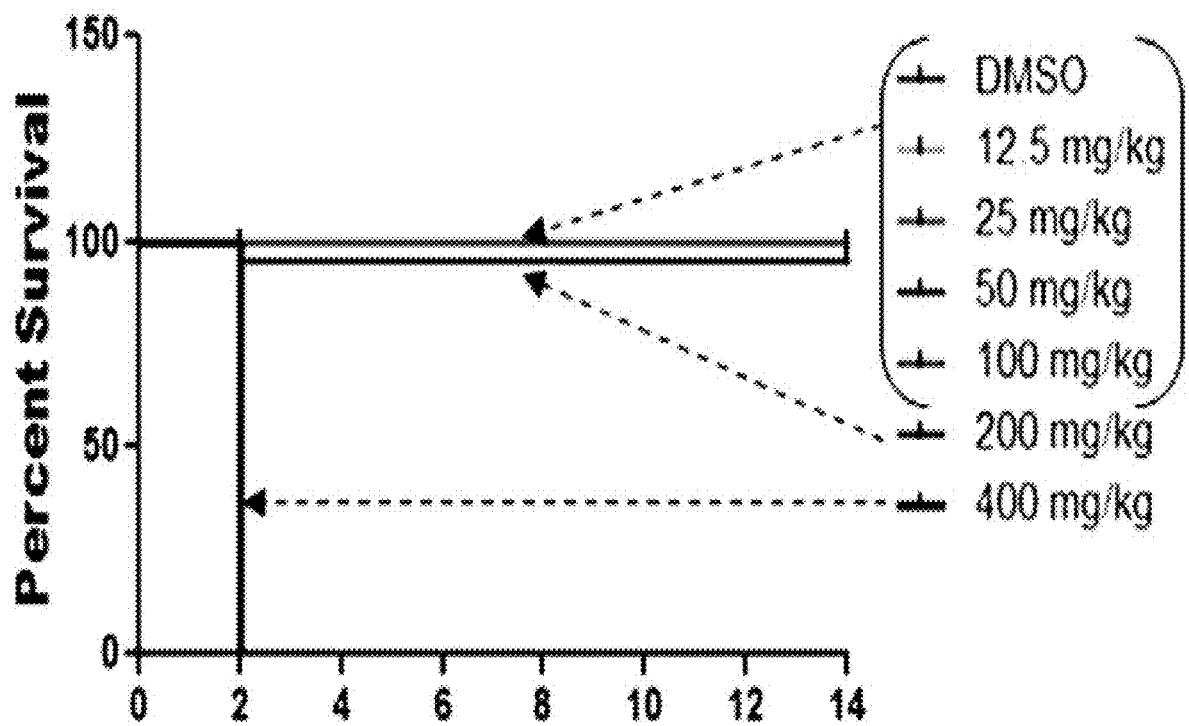

Eighty naive C57BL/6 male mice (at least 9 weeks of age, 23 to 28 g) were randomly assigned to groups (n=10) and dosed with 12.5-400 mg/ml Q3G or 10% DMSO in a single 5 ml intraperitoneal injection (FIG. 3A). Changes in body weight were monitored for 14 days as an indication of toxicity.

Quantification of VSV and VSV-Ebola Virus Inhibition by Q3G

Vero E6 cells were pre-treated with 10 µM Q3G or DMSO for 1 hour at 37° C. and infected with an MOI=0.1 of VSV, VSV-EBOV, VSV-SUDV or VSV-RESTV for 1 hour at 37° C. Cells were then overlaid with fresh medium. Some experiments included Q3G after viral adsorption and some were done in the absence of Q3G after adsorption. At 72 h, supernatants were harvested and titered on Vero E6 cells using a TCID$_{50}$ assay.

Effect of Q3G on Viral Infectivity

200 µl of VSV, VSV-EBOV, VSV-SUDV and VSV-RESTV viral stocks were treated with 10 µM Q3G or DMSO for 1 hour at 37° C., purified using a 20% sucrose cushion (30,000×g, 4° C., 2 h) and resuspended in 200 µl PBS. The purified virus was then titered using a TCID50 assay.

Statistics

Differences in survival were calculated for Q3G groups compared to DMSO using a log-rank (Mantel-Cox) test in Prism™ 5. Unpaired, two-sided t-tests with Welch's correction were performed to determine differences between DMSO and Q3G treatment groups in vitro. *=p-value <0.05; =p-value <0.01, *=p-value <0.001.

Effect of Q3G on the Activity of Cathepsins B and L

Vero E6 cells were grown to 95% confluence and treated with a range of doses of Q3G (0-100 µM) for 1 hour and assessed for cathepsins B and L activity using the Cathepsin Activity Assay (Abcam) kits and following the manufacturer's instructions.

Effect of Q3G on Acidification of Lysosomes

Vero E6 cells were grown to 85% confluence, treated with a range of doses of Q3G (0-100 µM) for 1 hour and stained with 100 nM Lysotracker™ Red DND-99 (ThermoFisher Scientific) for 30 minutes at 37° C. Live images were taken with an EVOS™ microscope at 10× magnification.

Figure 1B:
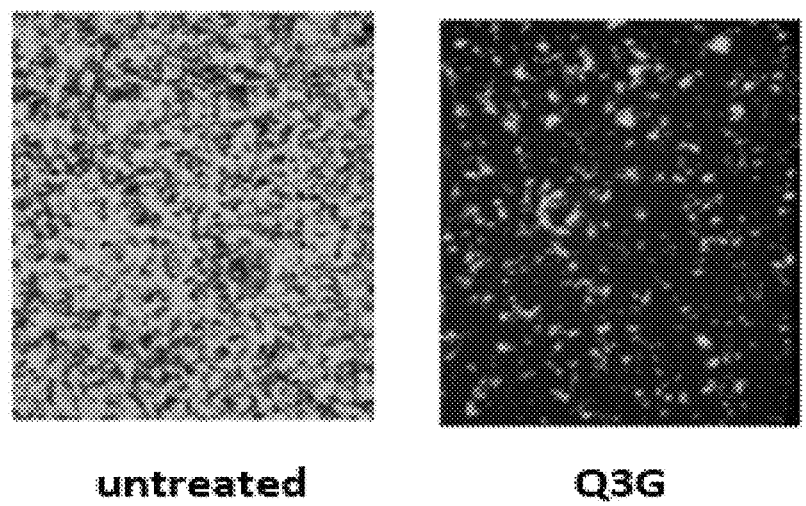
Figure 1C:
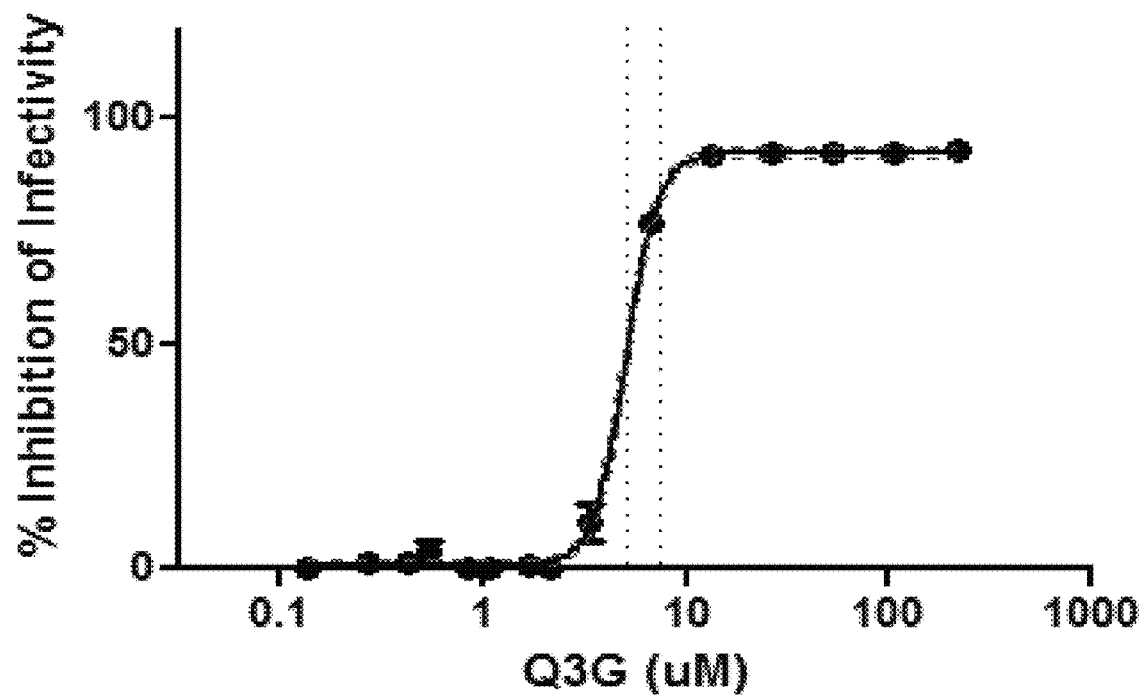
Figure 1D:
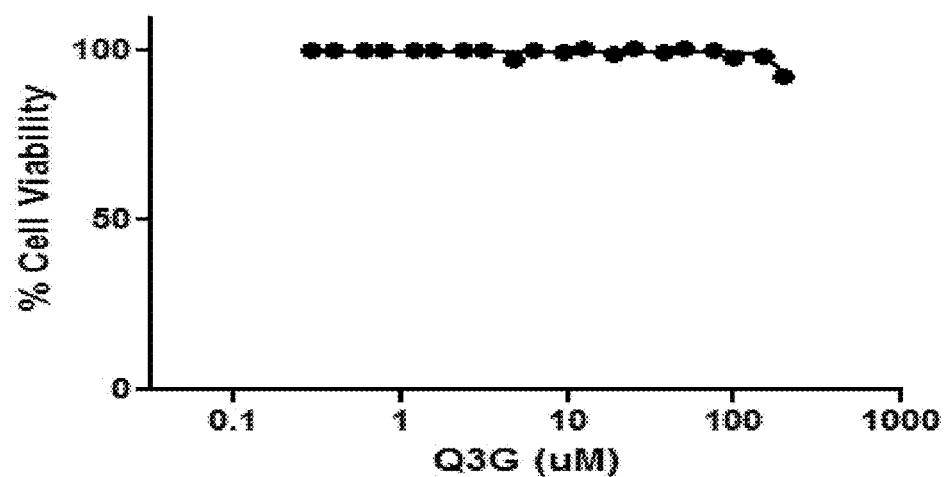
Figure 1E:
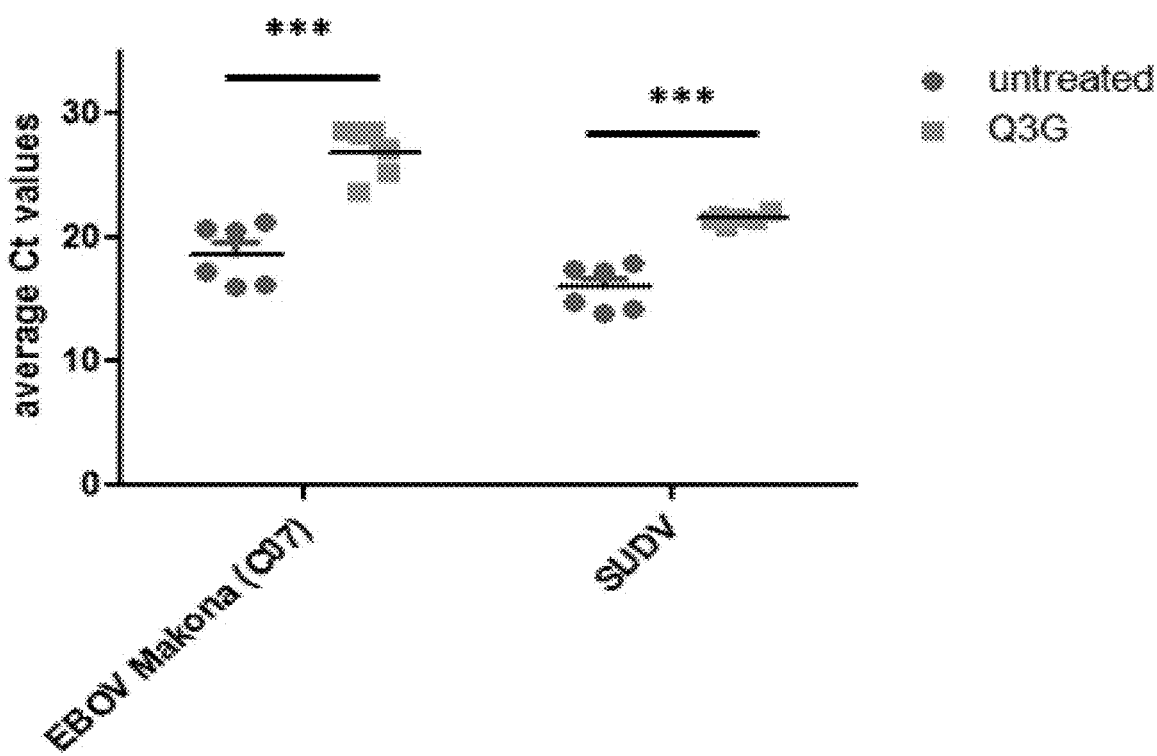
Figure 1F:
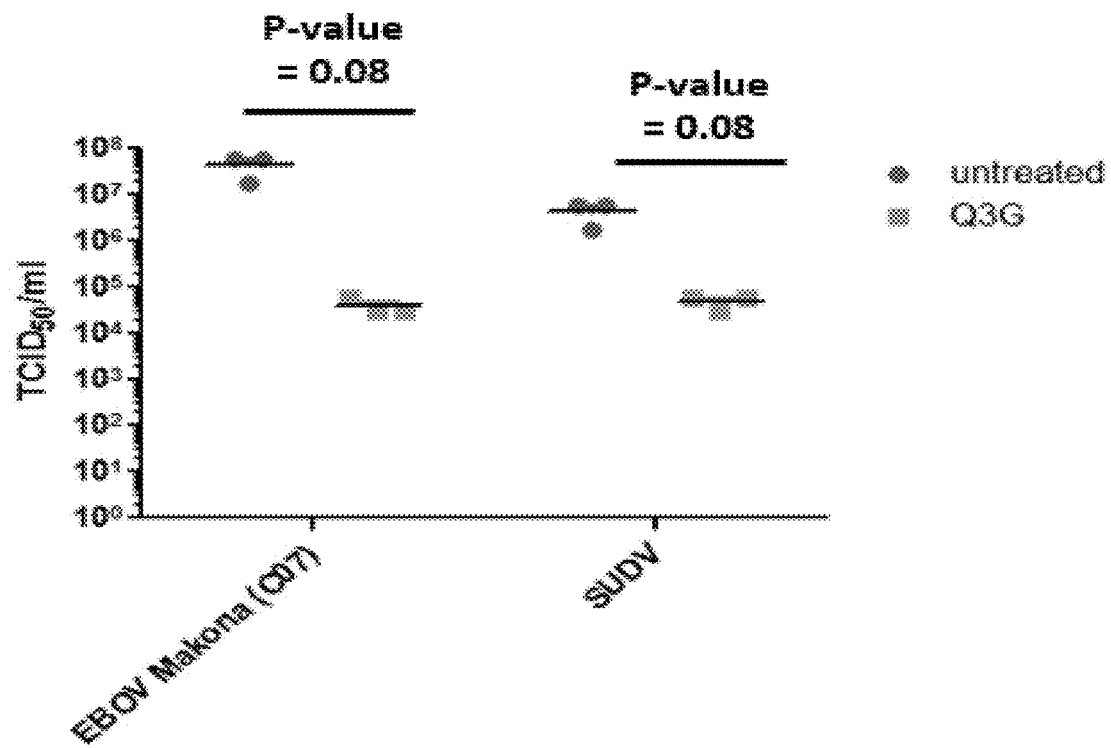

Example 2: In Vitro Antiviral Activity of Q3G Against Multiple Wildtype Ebolaviruses In order to test the antiviral activity of this compound against ebolavirus, the half maximal effective concentration (EC$_{50}$) and 90% of maximal effective concentration (EC$_{90}$) values were first calculated using Vero E6 epithelial cells. Cells were pre-treated with 2-fold dilutions of Q3G for 1 hour and infected with an enhanced GFP-expressing EBOV virus at an MOI of 0.1 for 1 hour in the presence of Q3G. The infected cells were incubated in the presence of Q3G for three days, after which fluorescent images were taken of each Q3G dilution (one dilution represented in FIG. 1B) and the fluorescence was quantified using a Bio-Tek™ plate reader. This produced a curve from which the EC$_{50}$ and EC$_{90}$ values were calculated to be 5.3 µM (CI+/−0.32) and 9.3 µM, respectively (FIG. 1C). Importantly, the decrease in viral titers could not be attributed to the toxicity of Q3G, as the cells exhibited 100% viability at all concentrations tested (FIG. 1D). In addition, it was confirmed that Q3G also inhibited replication of other variants and viruses of the Ebola genus including wildtype EBOV-Makona and SUDV-Boniface using RT-qPCR (FIG. 1E) and a TCID$_{50}$ assay (FIG. 1F). Collectively, these data demonstrate the in vitro antiviral activity of Q3G against multiple wildtype ebolaviruses.

Figure 2A:
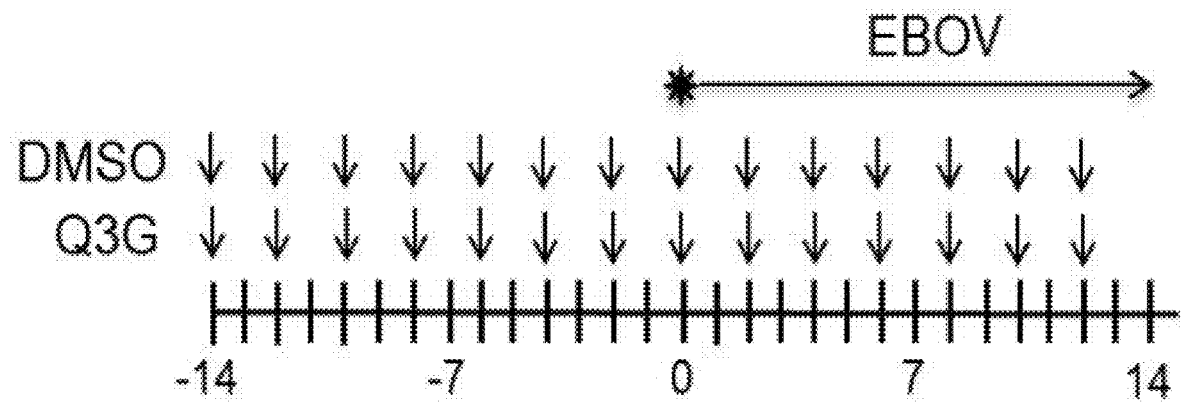
Figure 2B:
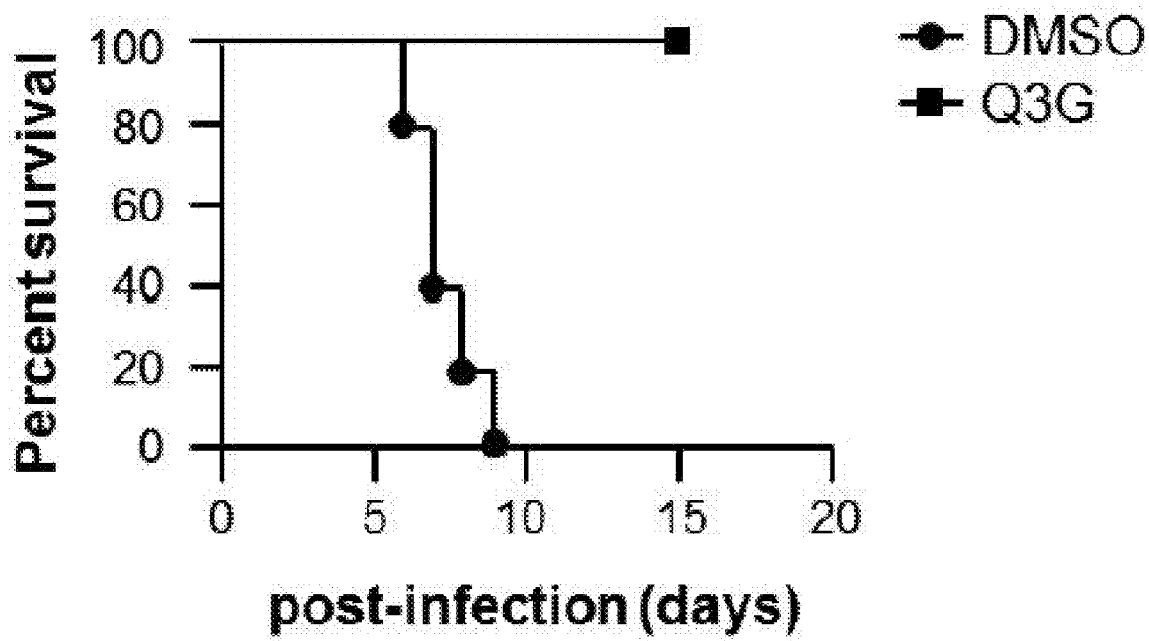
Figure 2C:
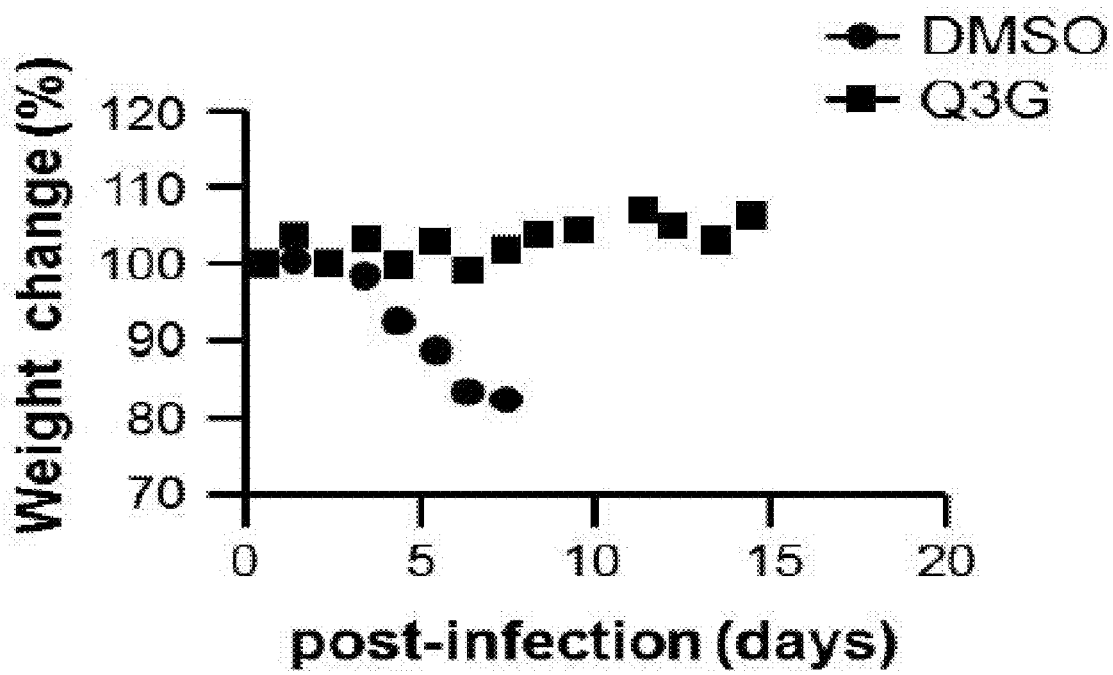
Figures 2F, 2G:
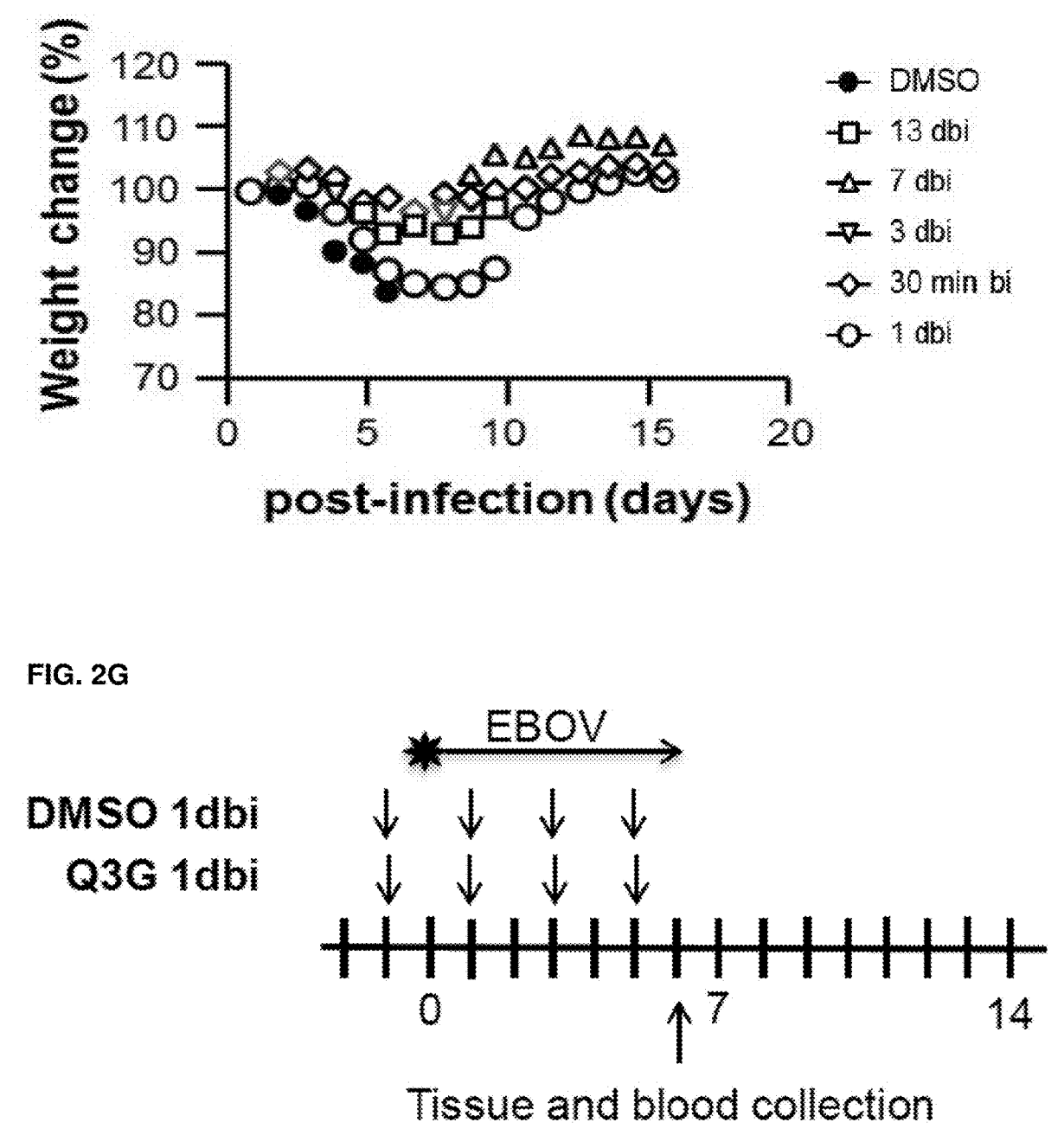
Figure 2H:
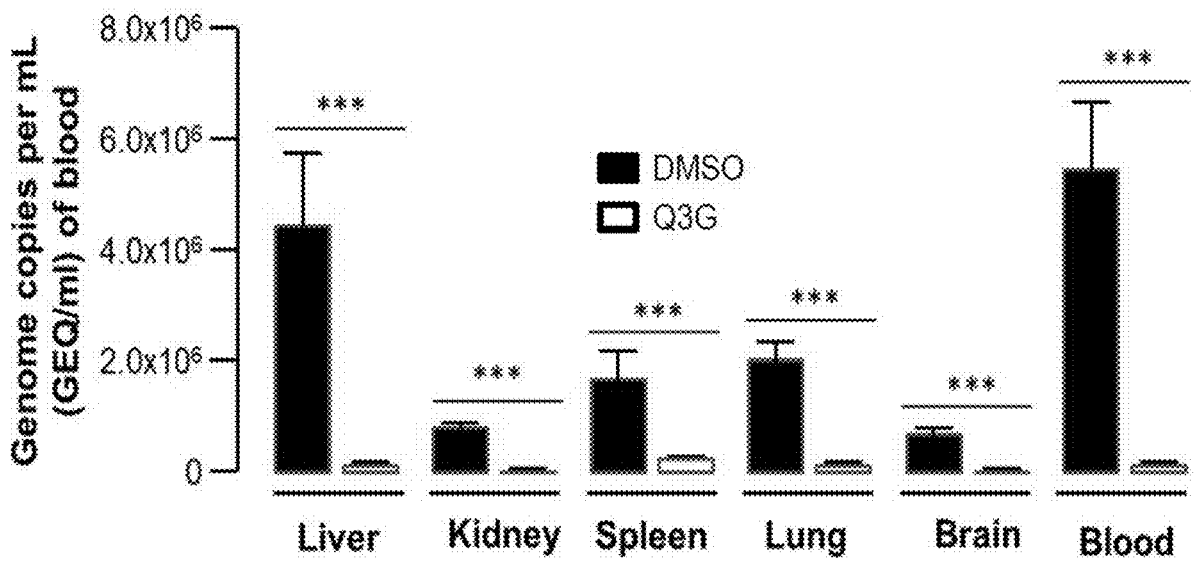

Example 3: In Vivo Antiviral Activity of Q3G Against Multiple Wildtype Ebolaviruses In order to test whether the antiviral activity observed in vitro would also be protective in vivo, a pilot experiment (n=10) was first performed in which C57BL/6 mice were treated with 50 mg/kg of Q3G every other day for 2 weeks followed by challenge with a lethal dose (1000×LD$_{50}$) of mouse-adapted Ebola virus (MA-EBOV). Q3G treatments were also continued every 48 h (every other day) after infection for an additional 12 days (FIG. 2A). All control animals succumbed to the viral challenge with a mean time to death of 7.4 days +/−1.1 while all Q3G-treated mice survived (FIG. 2B) and showed only mild signs of disease such as minimal weight loss (FIG. 2C). For the second experiment, the robustness of Q3G efficacy was tested by using Balb/c mice, which have a different genetic background and immune response from C57BL/6 mice. In addition to 2 weeks pre-treatment, shorter pretreatment times were also used including 13 d, 7 d, 3 d and 30 min as well as one post-treatment time at 24 h post infection (1 d) (FIG. 2D). Q3G treatments were also continued every 48 h after infection until day 11 (FIG. 2D). It was found that Q3G fully protected mice against viral challenge even when given only 30 minutes prior to infection (FIG. 2E) and resulted in less than 10% weight loss (FIG. 2F). In contrast, only 3/10 mice that received Q3G at 24 hours post challenge survived (FIG. 2E) and had significant weight loss of 20% (FIG. 2F).

Example 4

Next was investigated whether lower prophylactic doses of Q3G or higher post-exposure doses would be equally or more protective. A toxicity assay was first carried out in which groups of mice (n=10) were given a single intraperitoneal injection of different doses of Q3G (0-400 mg/kg) and then weighed and scored daily to monitor signs of toxicity. All mice that received 400 mg/kg died within 2 days (FIG. 3A). One mouse that received 200 mg/kg died on day 2 as well, and the others lost ~15% weight within the first 3 days but then recovered (FIG. 3B). All other mice survived and remained alert and active, without signs of toxicity (FIGS. 3A and 3B).

Figure 3D:
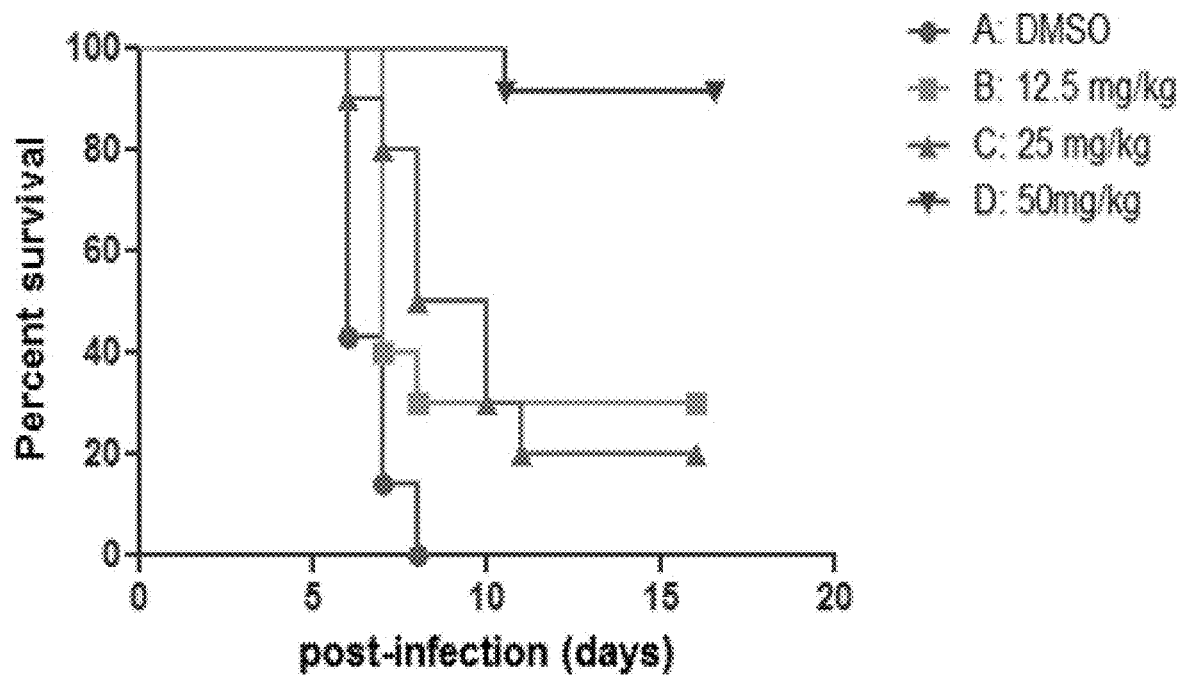
Figure 3E:
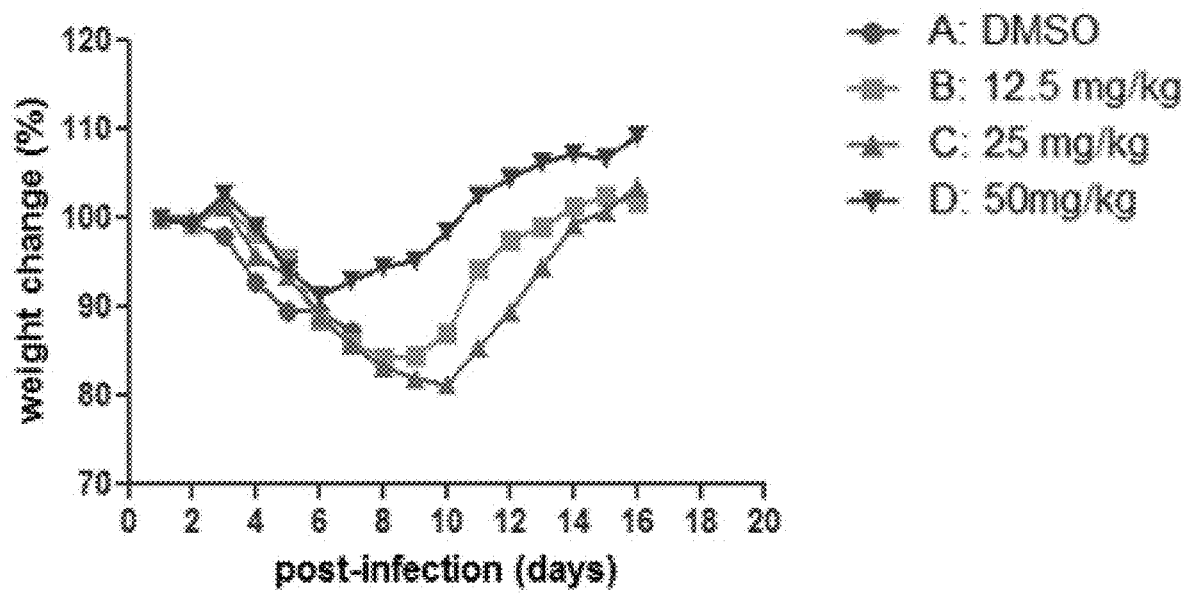
Figures 3H, 4A:
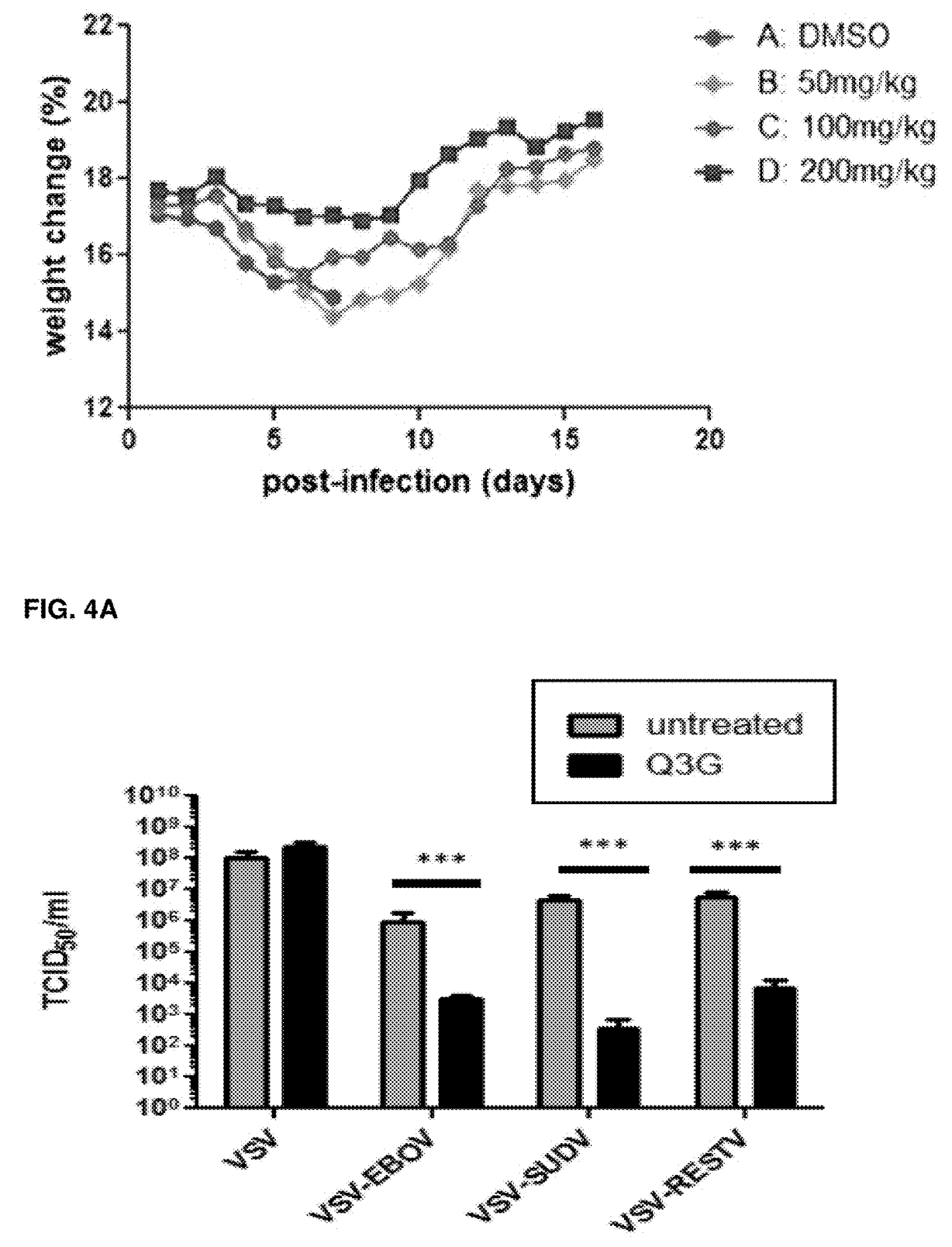

To test different prophylactic treatment concentrations, 12.5, 25 and 50 mg/ml Q3G were used (FIG. 3C). Compared to 9/10 mice surviving with 50 mg/kg Q3G (FIG. 3D) and minimal weight loss (FIG. 3E), both 25 mg/kg and 12.5 mg/kg Q3G resulted in 2/10 and 3/10 survival, respectively (FIG. 3D) and >20% weight loss (FIG. 3E). To test whether higher concentrations of Q3G would provide greater protection when given post exposure, mice were treated with 50, 100 and 200 mg/kg (this higher dose given on Day one only) Q3G (FIG. 3F). Surprisingly, all three doses resulted in similar survival rates of 4/10 or 5/10 mice and did not alter average time to death (FIG. 3G). Similarly, weight loss was not significantly different with higher doses of Q3G (FIG. 3H). Notably, 5/10 mice died on day 2 after treatment with 200 mg/kg Q3G and hence, treatment was discontinued.

Example 5: Mechanism of Q3G on Ebolavirus Replication

Figures 4B, 4C:
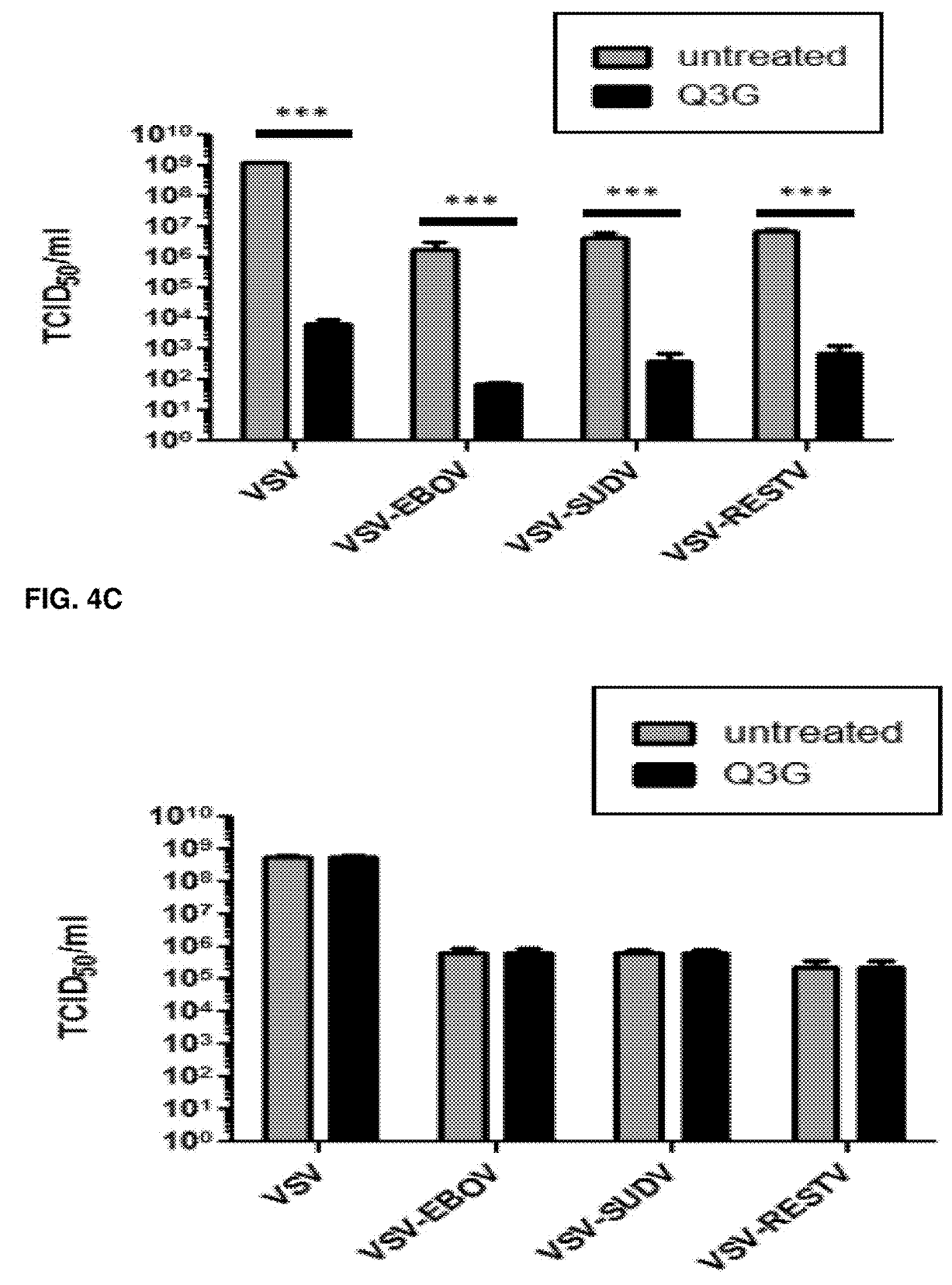
Figure 5A:
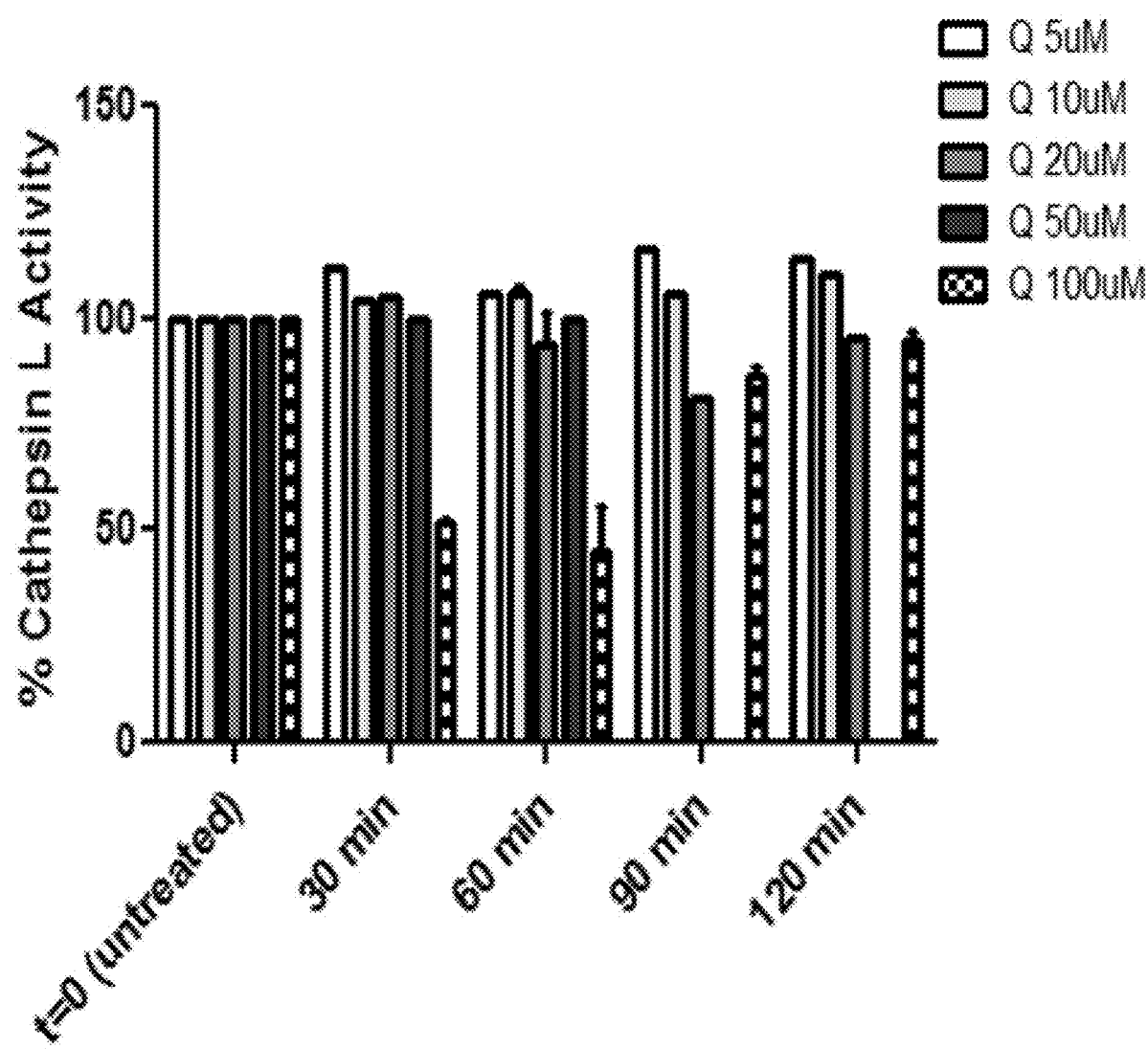
FIGS. 5A-B: Effect of Q3G on cathepsin L or B activity: Vero E6 cells were incubated with Q3G, lysed for cytoplasmic proteins and incubated with a fluorescent cathepsin substrate. The amount of cleaved substrate via (FIG. 5A) Cathepsin L and (FIG. 5B) Cathepsin B was measured with a fluorescent plate reader. All experiments were done in triplicate.
Figure 5B:
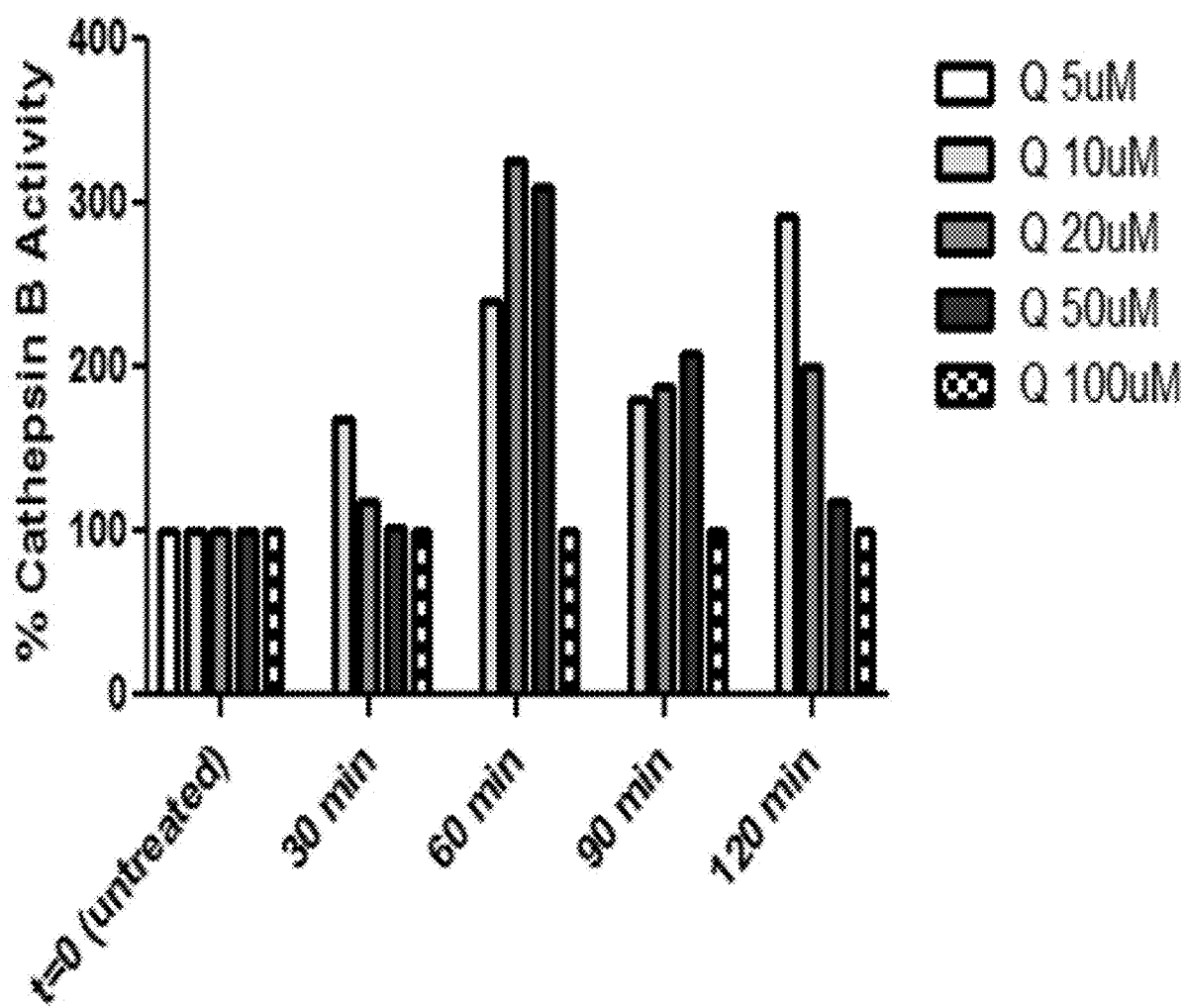
Figure 6:
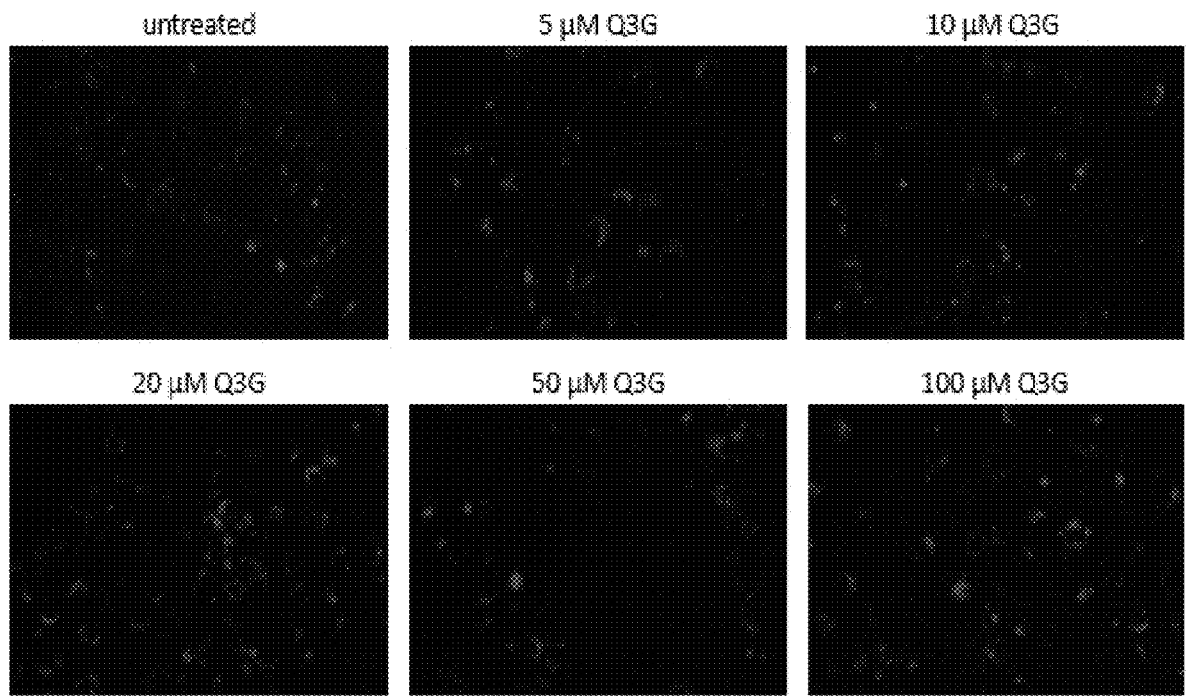
FIG. 6: Effect of Q3G on lysosomal pH: Vero E6 cells were grown to 85% confluence, treated with a range of doses of Q3G (0-100 μM) for 1 hour and stained with 100 nM Lysotracker for 30 minutes at 37° C. Live images were taken with an EVOS microscope at 10× magnification. All experiments were performed in duplicate.

It was investigated whether Q3G was effective at blocking ebolaviruses at an entry or post-entry step. Wildtype VSV and VSV-Ebola constructs were utilized in which the outer glycoprotein for VSV was replaced with the glycoprotein from ebolaviruses. Hence, this construct is equipped with the cell tropism and entry mechanisms of a filovirus but retains the VSV replication machinery. Adding Q3G only as a pre-treatment had no effect on wildtype VSV replication but strongly reduced the replication of multiple VSV-Ebola constructs including VSV-EBOV, VSV-SUDV and VSV-RESTV (FIG. 4A). However, if cells were pretreated and then kept in the presence of Q3G throughout the viral replication process, wildtype VSV titers decreased by 5 logs (FIG. 4B) and the pseudotyped VSV constructs displayed a further log reduction in titers (FIG. 4B). The inventors then proceeded to test several steps that had been previously shown to be important for ebolavirus entry including viral particle infectivity (FIG. 4C), cathepsin activity (FIGS. 5A and 5B) or lysosomal pH (FIG. 6) but did not find any effect of Q3G on any of these processes.

Example 6: Determination of Maximum Recommended Starting Dose for Human

The allometric scaling method of Mahmood et al. (Mahmood, 2003) can be used to extrapolate the dose from mice to human.

The maximum recommended starting dose (MRSD) for human is calculated by establishing the No Observed Adverse Effect Level (NOAEL, see Guidance for Industry and Reviewers. December 2002). Various concentrations of the formulation described above have been tested on mice, including 12.5 mg/kg, 25 mg/kg, 50 mg/kg, 100 mg/kg, 200 mg/kg and 400 mg/kg. The NOAEL for mice was 100 mg/kg.

This dose was scaled up to a human equivalent dose (HED) using published conversion tables which provide a conversion factor from mice to human of 12.3. A NOAEL of 100 mg/kg for mice is equivalent to 8.13 mg/kg in human (see also Nair et al. 2016).

This value (8.13 mg/kg) was divided by a security factor of ten. The calculated MRSD is thus 0.813 mg/kg. For an average human weighting 70 kg, a daily dose of 56.91 mg (i.e. about 57 mg) could thus be administered to start clinical trials.

Example 7: In Vitro Antiviral Activity of Q3G Against Zika Viruses

Figure 7A:
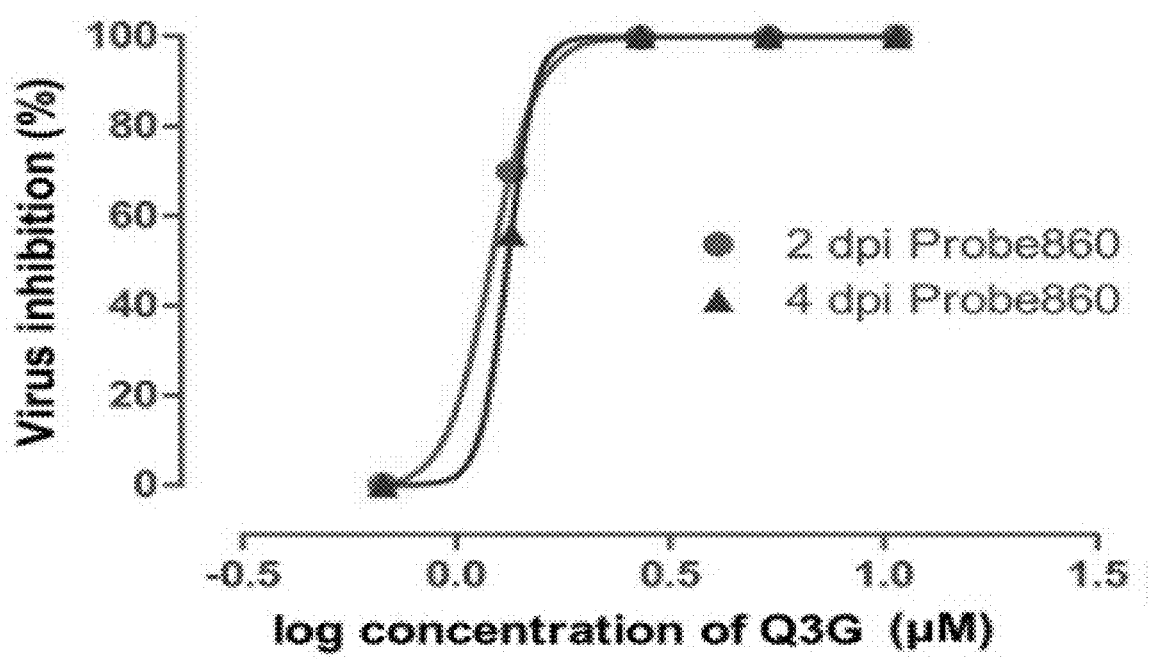
FIGS. 7A-C: Antiviral activity of Q3G against ZIKV in cell culture. Viral inhibition curves of Q3G at various concentrations on ZIKV PLCal_ZV assessed at (FIG. 7A) 2 days post-infection (2 dpi) (circles) or 4 days post-infection (4 dpi) (triangles). Quantification of ZIKV nonstructural protein 1 NS1 expression by ELISA from the (FIG. 7B) supernatant and (FIG. 7C) cell lysate of Vero cells infected with PLCal_ZV and treated with Q3G at various concentrations. The term "mock" indicates mock infection. All experiments were performed in triplicate and error bars represent mean±standard deviation. P<0.01; *P<0.001.
Figure 8:
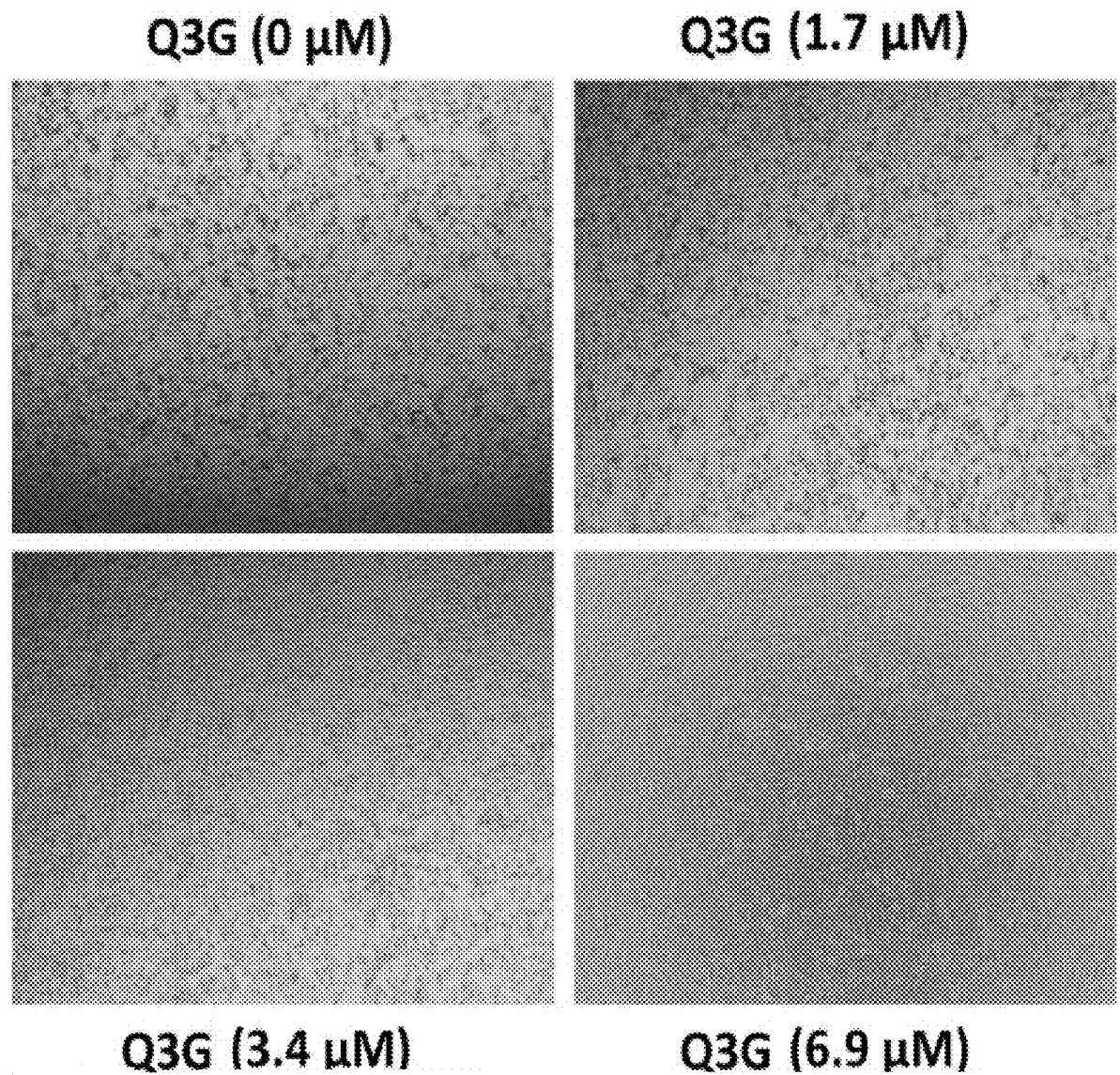
FIG. 8: Inhibitory effect of Q3G at the indicated concentrations on ZIKV PLCal_ZV (MOI=0.05) in Vero cells, and visualized under a microscope at 4 dpi.

Vero cells were pre-treated with various concentrations of Q3G or DMSO as a control for 1 hour at 37° C., and infected at a multiplicity of infection (MOI) of 0.05 with PLCal_ZV in the presence of the corresponding concentration of Q3G. After 1 hour, the inoculum was removed, and MEM supplemented with 1% penicillin-streptomycin, 1% fetal bovine serum, and the corresponding concentration of Q3G. Viral RNA was extracted from the supernatant using the QIAamp™ viral RNA minikit (Qiagen) at either 2- or 4-day post-infection (dpi) and quantified by RT-qPCR using the LightCycler™ 480 RNA Master Hydrolysis Probes kit (Roche, 04991885001) and a primer-probe set (Probe860) as published previously (Lanciotti, 2008). Reaction conditions were 63° C. for 3 minutes, 95° C. for 30 seconds, and then 45 cycles of 95° C. for 15 seconds and 60° C. for 30 seconds on an ABI Step OnePlus™ thermocycler. Q3G results were normalized to the control (which was set at 0% inhibition). The 50% effective concentration ($EC_{50}$) and 90% effective concentrations ($EC_K$) values were calculated using a four-parameter logistic regression in Prism5™ (GraphPad). The $EC_{50}$ and $EC_{90}$ of Q3G against PLCal_ZV were approximately 1.2-1.3 µM and 1.5 µM, respectively, when assessed on both 2 and 4 dpi (FIG. 7A). Q3G-based inhibition on PLCal_ZV (MOI=0.05) in Vero cells was also confirmed visually under the microscope, in which complete inhibition of cytopathic effects (CPE) was observed at a concentration of 6.9 µM at 4 dpi (FIG. 8).

Figure 7B:
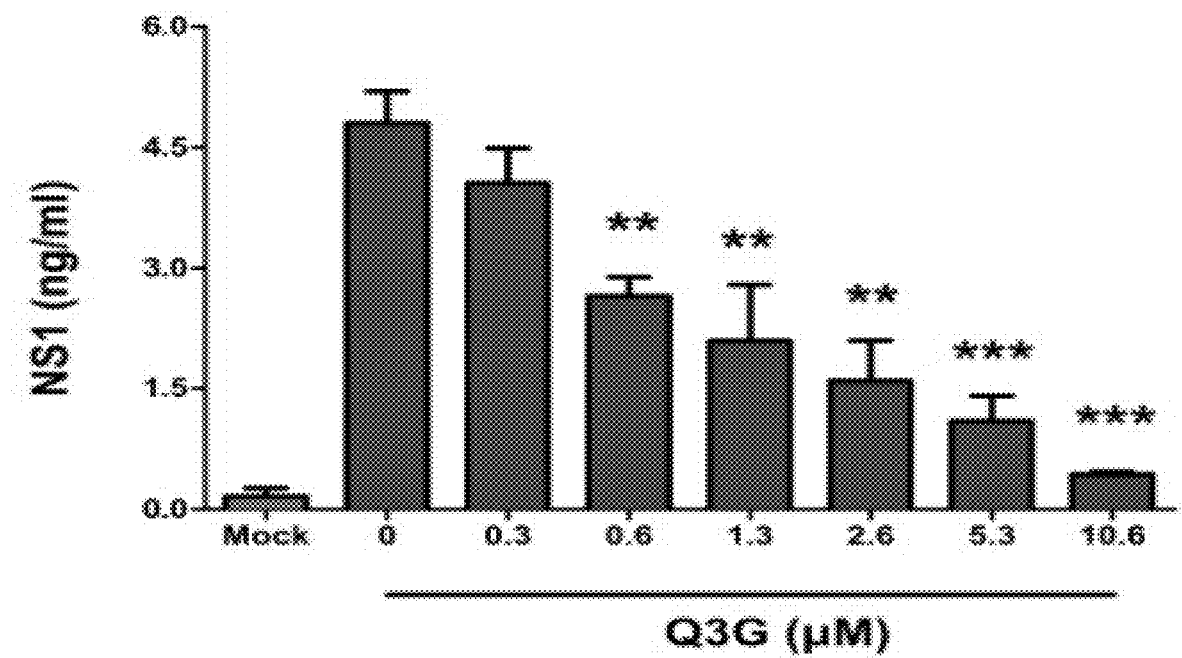
Figure 7C:
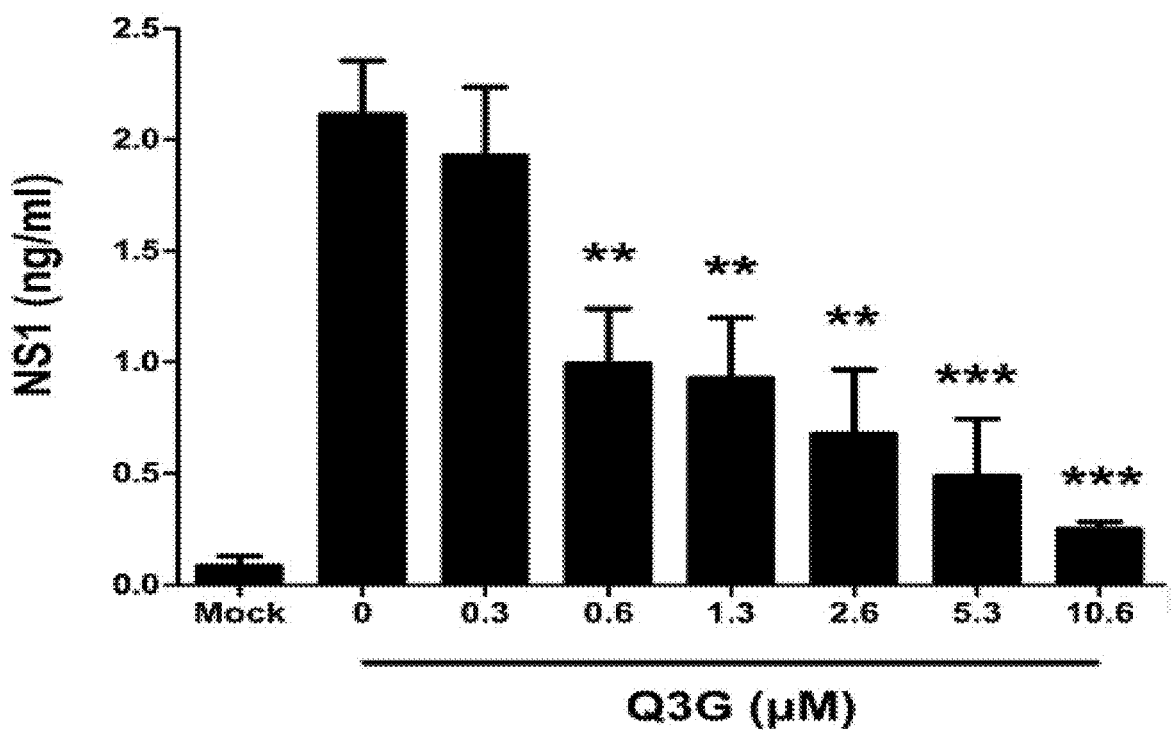

The same in vitro infection conditions were used to quantify the expression of ZIKV nonstructural protein 1 (NS1) at 4 dpi as a means to estimate virus replication at the protein level. Using an anti-ZIKV NS1 ELISA kit (BioFront Technologies, ZIKV-NS-1-EK), it was shown that Q3G inhibited replication of PLCal_ZV in a dose-dependent manner, as evidenced by the decrease in NS1 in both the cell supernatant and lysate, with statistically significant (as determined by Student's t-test) reductions observed at concentrations of 0.6 µM and over (FIGS. 7B and 7C).

Example 8: In Vivo Antiviral Activity of Q3G Against Zika Viruses—Therapy

Figure 9A:
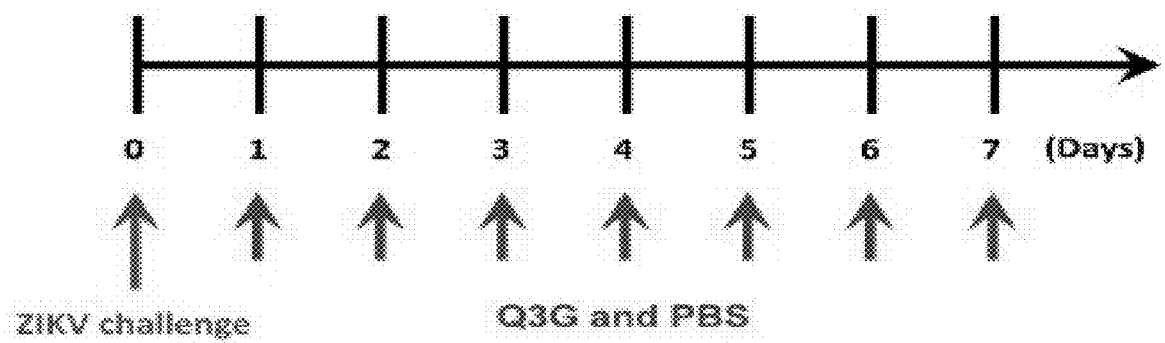
FIGS. 9A-C: Treatment of ZIKV-infected Ifnar1−/− mice with Q3G.
Figure 9B:
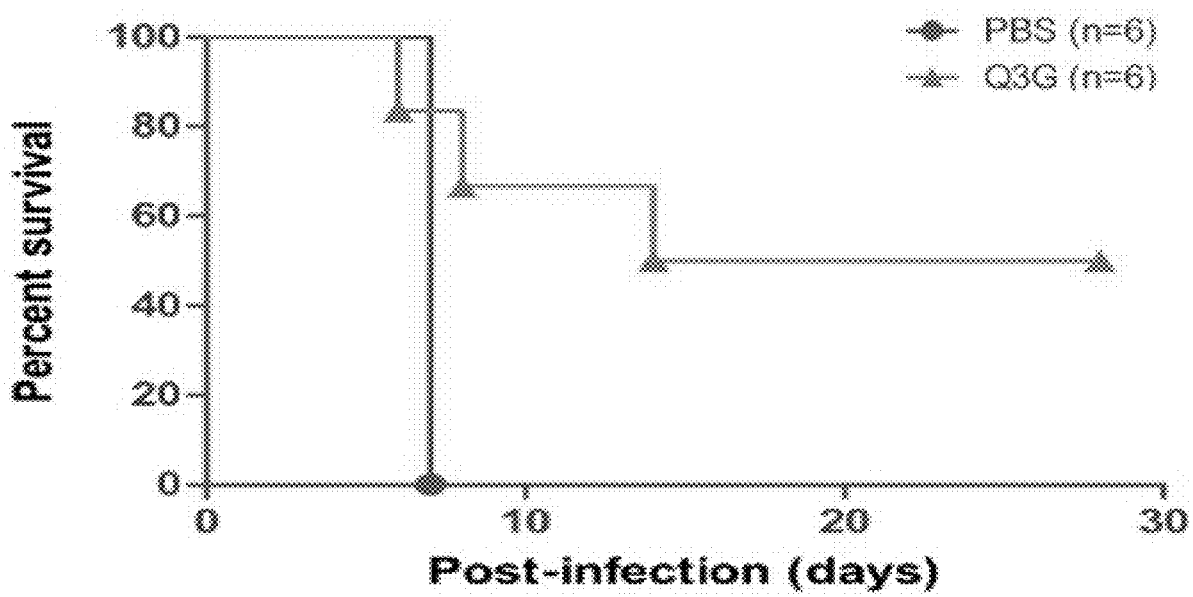
Figure 9C:
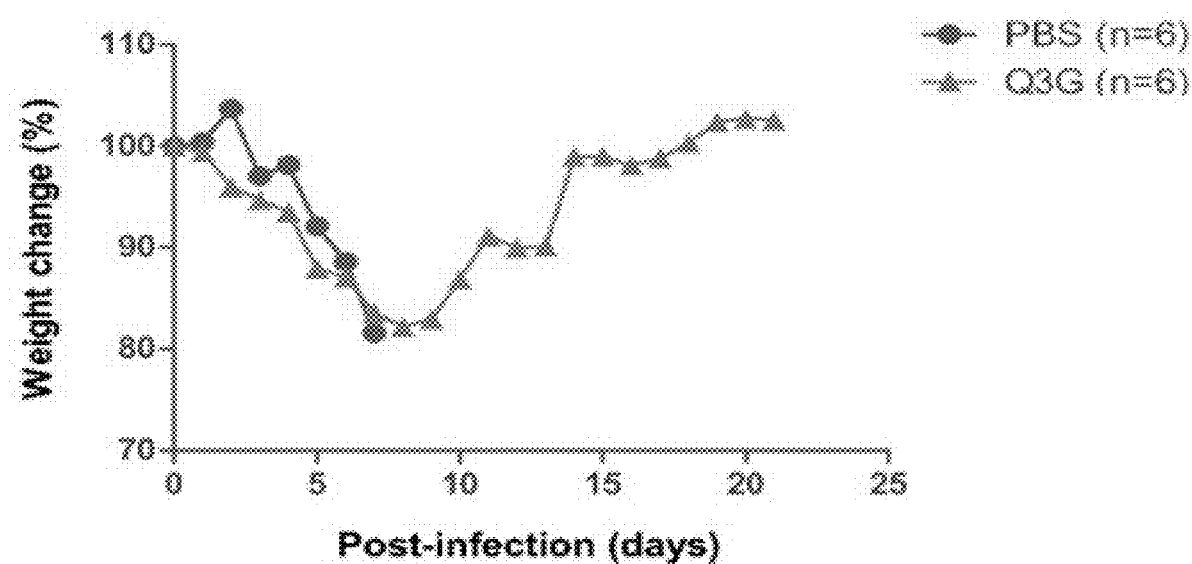

The therapeutic efficacy of Q3G was then tested in immunocompromised mice (Ifnar1$^{-/-}$, which were previously shown to be susceptible to ZIKV infection (Lazear, 2016). Using the PRVABC59 isolate of ZIKV, 6 to 8-week-old, male or female Ifnar1$^{-/-}$ mice (n=6 per group) were infected intraperitoneally (IP) with $1 \times 10^6$ plaque forming units (PFU) of the virus per animal (day 0) and observed daily for survival and weight loss. Q3G was administered via IP at a dose of 50 mg/kg beginning at 1 day after challenge (day 1) and continued every day for 7 days. Control animals were given the same volume of PBS under the same regimens (FIG. 9A). The control animals uniformly succumbed to ZIKV infection at 7 dpi with an average of ~20% weight loss at the time of death (FIGS. 9B and 9C). Post-exposure administration of Q3G was partially effective, with 50% of animals surviving the infection and an average weight loss of ~20% (FIGS. 9B and C).

Example 9: In Vivo Antiviral Activity of Q3G Against Zika Viruses—Prophylaxis The preventive efficacy of Q3G is tested in immunocompromised mice (Ifnar1$^{-/-}$). Q3G is administered to 6 to 8-week-old, male or female Ifnar1$^{-/-}$ mice (n=6 per group) via IP at a dose of 50 mg/kg beginning at 1 day (at day −14) and continued every day until day 12. Control animals are given the same volume of PBS under the same regimens. On day 0, using the PRVABC59 isolate of ZIKV, both groups are infected intraperitoneally (IP) with $1 \times 10^6$ plaque forming units (PFU) of the virus per animal and observed daily for survival and weight loss.

Example 10: In Vivo Antiviral Activity of Q3G Against Ebola and Zika Viruses The therapeutic and preventive efficacy of Q3G is tested in monkey using the methods described above with adaptations.

Example 11: In Vitro Antiviral Activity of EMIQ Against Ebola and Zika Viruses Experiments described in Examples 2 to 10 are performed using the Q3G analogue EMIQ.

The scope of the claims should not be limited by the preferred embodiments set forth in the examples, but should be given the broadest interpretation consistent with the description as a whole.

REFERENCES

Cao-Lormeau, V. M., Blake, A., Mons, S., Lastere, S., Roche, C., Vanhomwegen, J., Dub, T., Baudouin, L., Teissier, A., Larre, P., Vial, A. L., Decam, C., Choumet, V., Halstead, S. K., Willison, H. J., Musset, L., Manuguerra, J. C., Despres, P., Fournier, E., Mallet, H. P., Musso, D., Fontanet, A., Neil, J., Ghawche, F., 2016. Guillain-Barre Syndrome outbreak associated with Zika virus infection in French Polynesia: a case-control study. Lancet 387, 1531-1539.

Carteaux, G., Maquart, M., Bedet, A., Contou, D., Brugieres, P., Fourati, S., Cleret de Langavant, L., de Broucker, T., Brun-Buisson, C., Leparc-Goffart, I., Mekontso Dessap, A., 2016. Zika Virus Associated with Meningoencephalitis. N Engl J Med 374, 1595-1596.

Côté M, Misasi J, Ren T, Bruchez A, Lee K, Filone C M, Hensley L, Li Q, Ory D, Chandran K, Cunningham J. Properties of replication-competent vesicular stomatitis virus vectors expressing glycoproteins of filoviruses and arenaviruses. J Virol, 2004. 78(10): p. 5458-65.

Furuta Y, Gowen B B, Takahashi K, Shiraki K, Smee D F, Barnard D L. 2013. Favipiravir (T-705), a novel viral RNA polymerase inhibitor. Antiviral Res 100(2): p. 446-54.

Govero, J., Esakky, P., Scheaffer, S. M., Fernandez, E., Drury, A., Platt, D. J., Gorman, M. J., Richner, J. M., Caine, E. A., Salazar, V., Moley, K. H., Diamond, M. S., 2016. Zika virus infection damages the testes in mice. Nature 540, 438-442.

Johansen L, Brannan J, Delos S, Shoemaker C, Stossel A, Hoffstrom B, DeWald L, Shornberg K, Scully C, Lehar J, Hensley L, White W, Olinger G. 2013. FDA-approved selective estrogen receptor modulators inhibit ebola virus infection. Sci Transl Med 5(190):190ra79.

Julander J G, Bantia S, Taubenheim B R, Minnin D M, Kotian P, Morrey J D, Smee D F, Sheridan W P, Babu Y S. 2014. BCX4430, a novel nucleoside analog, effectively treats yellow fever in a Hamster model. Antimicrob Agents Chemother 58(11): p. 6607-14.

Kawiecki, A. B., Christofferson, R. C., 2016. Zika Virus-Induced Antibody Response Enhances Dengue Virus Serotype 2 Replication In Vitro. J Infect Dis 214, 1357-1360.

Lanciotti, R. S., Kosoy, O. L., Laven, J. J., Velez, J. O., Lambert, A. J., Johnson, A. J., Stanfield, S. M., Duffy, M. R., 2008. Genetic and serologic properties of Zika virus associated with an epidemic, Yap State, Micronesia, 2007. Emerg Infect Dis 14, 1232-1239.

Lazear, H. M., Govero, J., Smith, A. M., Platt, D. J., Fernandez, E., Miner, J. J., Diamond, M. S., 2016. A Mouse Model of Zika Virus Pathogenesis. Cell Host Microbe 19, 720-730.

Ma, W., Li, S., Ma, S., Jia, L., Zhang, F., Zhang, Y., Zhang, J., Wong, G., Zhang, S., Lu, X., Liu, M., Yan, J., Li, W., Qin, C., Han, D., Wang, N., Li, X., Gao, G. F., 2016. Zika Virus Causes Testis Damage and Leads to Male Infertility in Mice. Cell 167, 1511-1524 e1510.

Madelain V, Oestereich L, Graw F, Nguyen T H T, de Lamballerie X, Mentré F, Günther S. Guedj J. 2015. Ebola virus dynamics in mice treated with favipiravir. Antiviral Res 123: p. 70-77.

Mahmood I, Green M D, & Fisher J E 2003 Selection of the First-Time Dose in Humans: Comparison of Different Approaches Based on Interspecies Scaling of Clearance. *J. Clin. PharmacoL,* 43 (7), 692-7.

Mansuy, J. M., Pasquier, C., Daudin, M., Chapuy-Regaud, S., Moinard, N., Chevreau, C., Izopet, J., Mengelle, C., Bujan, L., 2016. Zika virus in semen of a patient returning from a non-epidemic area. Lancet Infect Dis 16, 894-895.

Mlakar, J., Korva, M., Tul, N., Popovic, M., Poljsak-Prijatelj, M., Mraz, J., Kolenc, M., Resman Rus, K., Vesnaver Vipotnik, T., Fabjan Vodusek, V., Vizjak, A., Pizem, J., Petrovec, M., Avsic Zupanc, T., 2016. Zika Virus Associated with Microcephaly. N Engl J Med 374, 951-958.

Murray, K. O., Gorchakov, R., Carlson, A. R., Berry, R., Lai, L., Natrajan, M., Garcia, M. N., Correa, A., Patel, S. M., Aagaard, K., Mulligan, M. J., 2017. Prolonged Detection of Zika Virus in Vaginal Secretions and Whole Blood. Emerg Infect Dis 23, 99-101.

Nair, A. B., Jacob, S., 2016. A simple practice guide for dose conversion between animals and human J Basic Clin Pharm. 7(2): 27-31.

Oestereich L, Lüdtke A, Wurr S, Rieger T, Muñoz-Fontela C, Günther S. 2014. successful treatment of advanced Ebola virus infection with T-705 (favipiravir) in a small animal modeL. Antiviral Research 105:17-21.

Picazo E and Giordanetto F. Small molecule inhibitors of ebola virus infection. Drug Discov Today, 2015. 20(2): p. 277-86.

Qiu X, Alimonti J, Melito L, Fernando L, Stroher U, Jones S. 2011. Characterization of Zaire ebolavirus glycoprotein-specific monoclonal antibodies. Clin Immunol 141 (2):218-27.

Rastogi, M., Sharma, N., Singh, S. K., 2016. Flavivirus N S1: a multifaceted enigmatic viral protein. Virol J 13, 131.

Richner, J. M., Himansu, S., Dowd, K. A., Butler, S. L., Salazar, V., Fox, J. M., Julander, J. G., Tang, W. W., Shresta, S., Pierson, T. C., Ciaramella, G., Diamond, M. S., 2017. Modified mRNA Vaccines Protect against Zika Virus Infection. Cell 168, 1114-1125 e1110.

Sakurai Y, Kolokoltsov A, Chen C, Tidwell M, Bauta W, Klugbauer N, Grimm C, Wahl-Schott C, Biel M, Davey R. 2015. Two-pore channels control Ebola virus host cell entry and are drug targets for disease treatment. Science 347(6225):995-998.

Ventura, C. V., Maia, M., Bravo-Filho, V., Gois, A. L., Belfort, R., Jr., 2016. Zika virus in Brazil and macular atrophy in a child with microcephaly. Lancet 387, 228.

Warren T K, Wells J, Panchal R G, Stuthman K S, Garze N L, Van Tongeren S A, Dong L, Retterer, CJ, Eaton B P, Pegoraro G, Honnold S, Bantia S, Kotian P, Chen X, Taubenheim B R, Welch L S, Minning D M, Babu Y S, Sheridan W P, Bavari S. 2014. Protection against filovirus diseases by a novel broad-spectrum nucleoside analogue BCX4430. Nature. 508(7496): p. 402-5.

Wong G. and Kobinger G P. 2015. Backs against the Wall: Novel and Existing Strategies Used during the 2014-2015 Ebola Virus Outbreak. Clin Microbiol Rev 28(3): p. 593-601.

Xia T, Eiteman M A$^2$. 2017, Quercetin Glucoside Production by Engineered *Escherichia coli*. Appl Biochem Biotechnol. 2017 Jan. 19. doi: 10.1007/s12010-017-2403-x.

Zanluca, C., Melo, V. C., Mosimann, A. L., Santos, G. I., Santos, C. N., Luz, K., 2015. First report of autochthonous transmission of Zika virus in Brazil. Mem Inst Oswaldo Cruz 110, 569-572.

The invention claimed is:

1. A method of reducing the risk of filovirus hemorrhagic fever or a symptom thereof in a mammal host exposed to a filovirus, comprising administering an effective amount of quercetin-3 β-O-D-glucoside (Q3G), or a composition comprising Q3G and a pharmaceutically acceptable carrier, to said host prior to said exposure.

2. The method of claim 1, wherein the filovirus hemorrhagic fever or symptom thereof is Ebola virus disease (EVD) or a symptom thereof and the filovirus is an ebolavirus.

3. The method of claim 1, wherein the host is infected by the Zaire ebolavirus (EBOV).

4. The method of claim 1, wherein the host is infected by the Sudan ebolavirus (SUDV).

5. The method of claim 1, wherein the host is infected by the Reston ebolavirus (RESTV).

6. The method of claim 1, wherein Q3G, or the composition is administered to the host every other day beginning 13 days or less prior to said exposure and until 11 days after exposure.

7. The method of claim 1, wherein Q3G, or the composition is administered to the host every other day beginning 7 days or less prior to said exposure and until 11 days after exposure.

8. The method of claim 1, wherein the Q3G, or the composition is administered to the host every other day beginning 3 days or less prior to said exposure and until 11 days after exposure.

9. The method of claim 1, wherein Q3G, or the composition is administered to the host every other day beginning 1 days or less prior to said exposure and until 11 days after exposure.

10. The method of claim 1, wherein Q3G, or the composition is administered to the host every other day beginning 30 minutes or less prior to said exposure and until 11 days after exposure.

11. The method of claim 1, wherein the effective amount of Q3G or the analogue thereof is between about 0.8 mg/kg to 20 mg/kg, 0.8 mg/kg to 10 mg/kg, or 0.8 mg/kg to 8 mg/kg daily.

12. The method of claim 1, wherein the host is a human host.

13. The method of claim 1, wherein Q3G, or the composition is administered by an oral route.

14. The method of claim 1, wherein Q3G, or the composition is administered by a parenteral route.

15. The method of claim 1, wherein Q3G is administered.

16. A method of preventing or treating a Zika virus disease (ZVD) or a symptom thereof in a mammal host exposed to a Zika virus, comprising administering an effective amount of quercetin-3 β-O-D-glucoside (Q3G), or a composition comprising Q3G and a pharmaceutically acceptable carrier, to said host after said exposure.

17. The method of claim 16, wherein Q3G, or the composition is administered to the host every day for seven days beginning 1 day after said exposure.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: artificial sequence
<220> FEATURE:
<223> OTHER INFORMATION: Synthetic construct

<400> SEQUENCE: 1
cagccagcaa tttcttccat                                           20

<210> SEQ ID NO 2
<211> LENGTH: 20
<212> TYPE: DNA
<213> ORGANISM: artificial sequence
<220> FEATURE:
<223> OTHER INFORMATION: Synthetic construct

<400> SEQUENCE: 2
tttcggttgc tgtttctgtg                                           20

<210> SEQ ID NO 3
<211> LENGTH: 24
<212> TYPE: DNA
<213> ORGANISM: artificial sequence
<220> FEATURE:
<223> OTHER INFORMATION: Synthetic construct

<400> SEQUENCE: 3
atcattggcg tactggagga gcag                                      24

<210> SEQ ID NO 4
<211> LENGTH: 20
<212> TYPE: DNA
<213> ORGANISM: artificial sequence
<220> FEATURE:
<223> OTHER INFORMATION: Synthetic construct

<400> SEQUENCE: 4
cagaagacaa tgcagccaga                                           20

<210> SEQ ID NO 5
<211> LENGTH: 20
<212> TYPE: DNA
<213> ORGANISM: artificial sequence
<220> FEATURE:
<223> OTHER INFORMATION: Synthetic construct

<400> SEQUENCE: 5
ttgaggaata tcccacaggc                                           20

<210> SEQ ID NO 6
<211> LENGTH: 25
<212> TYPE: DNA
<213> ORGANISM: artificial sequence
<220> FEATURE:
<223> OTHER INFORMATION: Synthetic construct

<400> SEQUENCE: 6
ctgctagctt ggccaaagtc acaag                                     25
```